United States Patent
Al-Qahtani

(10) Patent No.: US 10,702,547 B2
(45) Date of Patent: Jul. 7, 2020

(54) COMPOSITIONS FOR TREATMENT OF ARTHRITIS

(71) Applicant: AQ SKIN SOLUTIONS INC., Irvine, CA (US)

(72) Inventor: Ahmed Al-Qahtani, Irvine, CA (US)

(*) Notice: Subject to any disclaimer, the term of this patent is extended or adjusted under 35 U.S.C. 154(b) by 139 days.

(21) Appl. No.: 15/981,057

(22) Filed: May 16, 2018

(65) Prior Publication Data

US 2019/0350967 A1     Nov. 21, 2019

(51) Int. Cl.
| | |
|---|---|
| *A61K 31/728* | (2006.01) |
| *A61K 38/18* | (2006.01) |
| *A61K 9/00* | (2006.01) |
| *A61P 19/02* | (2006.01) |
| *A61K 38/39* | (2006.01) |
| *A61K 35/51* | (2015.01) |
| *A61K 35/545* | (2015.01) |

(52) U.S. Cl.
CPC .......... *A61K 31/728* (2013.01); *A61K 9/0019* (2013.01); *A61K 35/51* (2013.01); *A61K 38/1825* (2013.01); *A61K 38/1841* (2013.01); *A61K 38/1866* (2013.01); *A61K 38/39* (2013.01); *A61P 19/02* (2018.01); *A61K 35/545* (2013.01); *A61K 2300/00* (2013.01); *A61L 2430/06* (2013.01); *A61L 2430/24* (2013.01)

(58) Field of Classification Search
CPC .............. A61K 31/728; A61K 38/1841; A61K 9/0019; A61K 2300/00; A61P 19/02
See application file for complete search history.

(56) References Cited

U.S. PATENT DOCUMENTS

| | | | | |
|---|---|---|---|---|
| 8,518,879 B2* | 8/2013 | Al-Qahtani | .......... | A61K 38/202 514/9.4 |
| 8,524,662 B2* | 9/2013 | Byers | ................. | A61K 38/1875 514/16.7 |
| 2010/0068180 A1* | 3/2010 | Marshall | .............. | C12N 5/0605 424/85.4 |
| 2018/0000736 A1* | 1/2018 | Martin | .................... | A61K 38/18 |
| 2018/0221411 A1* | 8/2018 | Vesey | ................. | A61K 35/545 |

* cited by examiner

*Primary Examiner* — Daniel C Gamett

(57) ABSTRACT

The present invention relates to compositions to treat inflammation, and more particularly, an injectable comprising hyaluronic acid and cell culture medium conditioned by cells grown in two-dimensional culture. Also included are methods of using such compositions and kits comprising the injectable therein.

20 Claims, 12 Drawing Sheets

COMPOSITIONS FOR TREATMENT OF ARTHRITIS

BACKGROUND OF THE INVENTION

Field of the Invention

The present invention is generally related to prevention and treatment of rheumatoid arthritis, and more specifically to a composition for medicaments for injection, comprising cell hyaluronic acid and culture medium conditioned by foreskin-derived fibroblast cells grown in two-dimensional culture.

Background Information

Arthritis is a common chronic disease that leads to joint ache due to the degeneration of articular cartilage or the inflammation of connective tissue, and thus, affects the normal movement of the joint. According to the location and causes of the occurrence, arthritis can be classified into more than a hundred types. The most common types comprise osteoarthritis (degenerative arthritis), rheumatoid arthritis, gouty arthritis, bacterial arthritis, ankylosing spondylitis, and lupus erythmatosus.

With regards to the therapy of arthritis, the initial therapy generally adopts conservative and non-surgical methods, such as medicine treatments and injection treatments. When the initial therapy is ineffective, a surgical operation treatment will then be adopted. It has been known that medicine treatments comprise the use of steroidal anti-inflammation drugs and non-steroidal anti-inflammation drugs. Although steroidal anti-inflammatory drugs can provide a quick and effective analgesic effect, the drugs cause many side effects, such as osteoporosis, uncicatrized wounds, upper gastrointestinal bleeding, or may even aggravate the symptoms of hypertension or diabetes. Thus, these drugs are gradually excluded in the medicine treatment. As for non-steroidal anti-inflammation drugs, although they can provide a good analgesic effect, if used long term, side effects, such as peptic ulcer, lower limb dropsy, damage of kidney function, etc., may arise. Thus, non-steroidal drugs are restricted in practical application.

HA is a non-sulfated glycosaminoglycan found in the extra cellular matrix of most cells, and increased amounts are found in connective, neural and epithelial tissues. Hyaluronic acid is made up of linear polymeric chains in which disaccharide units of N-acetylglucosamine and glucoronic acid, bonded via by glucoside bonds, are repeated. It has been reported to have roles in promoting contact inhibition through binding to the cell surface glycoprotein CD44. HA is widely used in supporting joint function in arthritis patients (such as via knee injections), beauty products, and veterinary medicine (knee injections for race horses).

It has been known that hyaluronic acid (also known as hyaluronan or alduronic acid) has been widely used in injection formulations for inhibiting osteoarthritis. In this case, an injection solution containing hyaluronic acid is directly injected into a patient's joint to moderately alleviate inflammation and relive the achy feeling. The mechanism of hyaluronic acid is still unclear to date, but it has been known that hyaluronic acid also can act as a lubricant to help the movement of joints, and meanwhile, improve joint function. However, it has been discovered that although hyaluronic acid can effetely relieve ache, when entering the human body, it is possible to induce temporary inflammatory responses within several days, or even may cause chronic inflammation (see Leopold et al., Increased frequency of acute local reaction to intra-articular hylan GF-20 (Synvisc) in patients receiving more than one course of treatment. J Bone Joint Surg, 2002; 84: 1619-23; Bernardeau et al., Acute arthritis after intra-articular hyaluronate injection: onset of effusions without crystal. Ann Rheum Dis, 2001; 60:518-20; and Kroesen et al., Induction of an acute attack of calcium pyrophosphate dihydrate arthritis by intra-articular injection of hylan GF 20 (Synvisc). Clin Rheumatol, 2000; 19:147-9, which are incorporated herein by reference in their entireties). Therefore, if a desired anti-inflammation effect can be provided by a lower dosage of hyaluronic acid, the subsequent inflammation responses induced after hyaluronic acid enters a human body can be alleviated or even can be avoided.

The high molecular weight of hyaluronic acid is an important pharmacological property. In many pharmaceutical applications it is undesirable to have low molecular weight hyaluronic acid in the formulation, for example in view of the inflammatory effects of low molecular weight HA as reported in U.S. Pat. No. 4,141,973 (herein incorporated by reference in its entirety) and the loss of beneficial reological properties of high molecular weight HA.

Growth factors are typically peptides with diverse biological effects. Some growth factor families that have been identified as useful in wound healing and/or epidermal remodeling include, e.g., transforming growth factor-ß (TGF-ß), epidermal growth factor (EGF), insulin-like growth factors (IGFs), platelet-derived growth factor (PDGF), and fibroblast growth factors (FGFs).

Living cells cultured in vitro secrete extracellular proteins and peptides, including growth factors, into the nutrient medium in which they are cultured. Medium exposed to cells in culture is referred to as "conditioned medium." Naughton et al., in U.S. Pat. No. 6,372,494, teach that conditioned medium from cell cultures comprising a three-dimensional extracellular matrix and multiple layers of stromal and tissue specific cells (i.e., a three-dimensional culture system) may be used advantageously to prepare growth factor-enriched cosmeceutical compositions; U.S. Pat. No. 6,372,494 is herein incorporated in its entirety by reference thereto. Indeed, Naughton et al. assert that the complex three-dimensional culture systems have numerous advantages over simple two-dimensional culture systems, e.g., greater surface area; more analogous to tissues in vivo; absence of "contact inhibition" (a limitation on the growth of cells in two-dimensional cultures); creation of localized microenvironments; increased cell-cell interactions and potential cell migration; maintenance of a differentiated phenotype and elaboration of differentiation factors, etc. Unfortunately, three-dimensional culture systems are substantially more expensive and technically challenging to establish and maintain than conventional two-dimensional culture systems. Moreover, the complex biological systems formed in three-dimensional culture create so many variables (e.g., cell-cell and cell-matrix interactions, tissue differentiation, etc.), that quality control with respect to the harvested conditioned medium becomes nearly impossible, and batch-to-batch variability in growth factor composition may be commercially unacceptable.

The inventors of the present invention found that a combination of conditioned media and hyaluronic acid can provide an improved anti-inflammation effect, including that a desired anti-inflammation effect may be provided by a lower dosage of hyaluronic acid, thereby alleviating or avoiding the temporary inflammation responses induced after hyaluronic acid enters the human body, where the formulations comprise conditioned medium enriched with growth factors and/or extracellular matrix compositions produced by economical, well-controlled and uniform two-dimensional cell culture methods.

SUMMARY OF THE INVENTION

The present invention relates to arthritis treatment compositions, comprising hyaluronic acid and cell culture medium conditioned by cells grown in two-dimensional culture. The present invention also discloses methods of using such compositions for the treatment of osteoarthritis.

In embodiments, an injectable composition for treating osteoarthritis is disclosed, including hyaluronic acid (HA) and a conditioned medium or extract or concentrate thereof, from cultured substantially homogenous fibroblast cells, where the conditioned medium is generated by incubating a nutrient medium with said cells in two-dimensional culture under conditions adapted to promote secretion of at least one growth factor into the nutrient medium, and where the at least one growth factor is present in said conditioned medium or extract or concentrate thereof in an amount sufficient to treat osteoarthritis symptoms.

In one aspect, the cells are from a cell line designated as ATCC Accession No. PTA-11680.

In another aspect, the hyaluronic acid is high molecular weight HA.

In one aspect, the at least one growth factor includes EGF, PDGF, FGF, TGF-β, TGF-α, NGF, Epo, IGF-I, IGF-II, IL-1-α, IL-1-β, IL-2, IL-3, IL-4, IL-5, IL-6, IL-7, IL-8, IL-9, IL-10, IL-11, IL-12, IL-13, INF-α, INF-β, INF-γ, TNF-α, TNF-β, GM-CSF, and M-CSFs, or a combination thereof.

In a related aspect, the combination comprises TGF Beta-1, TGF Beta-2, TGF Beta-3, IL-3, IL-6, IL-7, and IL-8, and where the conditioned media is present at a concentration between about 10% to about 20% (wt %).

In another related aspect, the combination comprises about 1-3 ng/mL TGF β-1, about 100-600 pg/mL TGF β-2, about 50-100 pg/mL TGF β-3, about 60 pg/mL IL-3, about 11 pg/mL IL6, about 50 pg/mL IL-7, and about 4-10 pg/mL IL-8, and wherein said conditioned media is present at about 10 to about 15 or at about 15 to 20% (wt %).

In one aspect, the composition further includes a pharmaceutically acceptable carrier.

In another aspect, the composition further includes a second conditioned medium or extract or concentrate thereof, where the second conditioned medium is generated by incubating a nutrient medium with a second substantially homogeneous eukaryotic cell type in two-dimensional culture under conditions adapted to promote secretion of at least one second growth factor or one or more extracellular matrix proteins, and wherein said growth factors or extracellular matrix proteins are present in the conditioned medium or extract or concentrate thereof in amounts sufficient to treat symptoms associated with osteoarthritis.

In one aspect, the symptoms include joint pain, joint stiffness, joint swelling, limited range of motion of joints, bony growths at the edge of joints, and combinations thereof.

In another aspect, the conditions comprise culturing of the cells with two-dimensional polysterene microcarriers.

In one embodiment, a kit is disclosed including the composition of as described above, a container, a label, and instructions which provide methods for injecting the composition.

In a related aspect, the kit further includes at least one preservative.

In another embodiment, a method of treating a symptom associated with osteoarthritis is disclosed including injecting into a joint of a subject in need thereof the composition as described above including a conditioned medium or extract or concentrate thereof, from cultured substantially homogenous foreskin derived fibroblast cells, where the conditioned medium is generated by incubating a nutrient medium with the cells in two-dimensional culture under conditions adapted to promote secretion of at least one growth factor into the nutrient medium, and where the at least one growth factor is present in the conditioned medium or extract or concentrate thereof in an amount sufficient to treat a symptom associated with osteoarthritis.

In a related aspect, the site of injection is the hips, knees, fingers, feet, toes or ankles.

In one aspect, a single injection is effective for at least a year.

In another aspect, the symptom includes joint pain, joint stiffness, joint swelling, limited range of motion of joints, bony growths at the edge of joints, and combinations thereof.

In one aspect, the at least one growth factor includes EGF, PDGF, FGF, TGF-β, TGF-α, NGF, Epo, IGF-I, IGF-II, IL-1-α, IL-1-β, IL-2, IL-3, IL-4, IL-5, IL-6, IL-7, IL-8, IL-9, IL-10, IL-11, IL-12, IL-13, INF-α, INF-β, INF-γ, TNF-α, TNF-β, GM-CSF, and M-CSFs, or a combination thereof.

In another aspect, the combination comprises TGF β-1, TGF β-2, TGF β-3, IL-3, IL-6, IL-7, and IL-8, and where the conditioned media is present at a concentration of at least about 10-20% (wt %).

In one aspect, 1-3 ng/mL TGF β-1, about 100-600 pg/mL TGF β-2, about 50-100 pg/mL TGF β-3, about 60 pg/mL IL-3, about 11 pg/mL IL6, about 50 pg/mL IL-7, and about 4-10 pg/mL IL-8, and where the conditioned media is present at about 10 to about 20% (wt %).

In another aspect, the composition contains a second conditioned medium or extract or concentrate thereof, where the second conditioned medium is generated by incubating a nutrient medium with a second substantially homogeneous eukaryotic cell type in two-dimensional culture under conditions adapted to promote secretion of at least one second growth factor or one or more extracellular matrix proteins, and where the growth factors or extracellular matrix proteins are present in the conditioned medium or extract or concentrate thereof in amounts sufficient to treat the symptom associated with osteoarthritis.

DETAILED DESCRIPTION OF THE INVENTION

Figure 1:
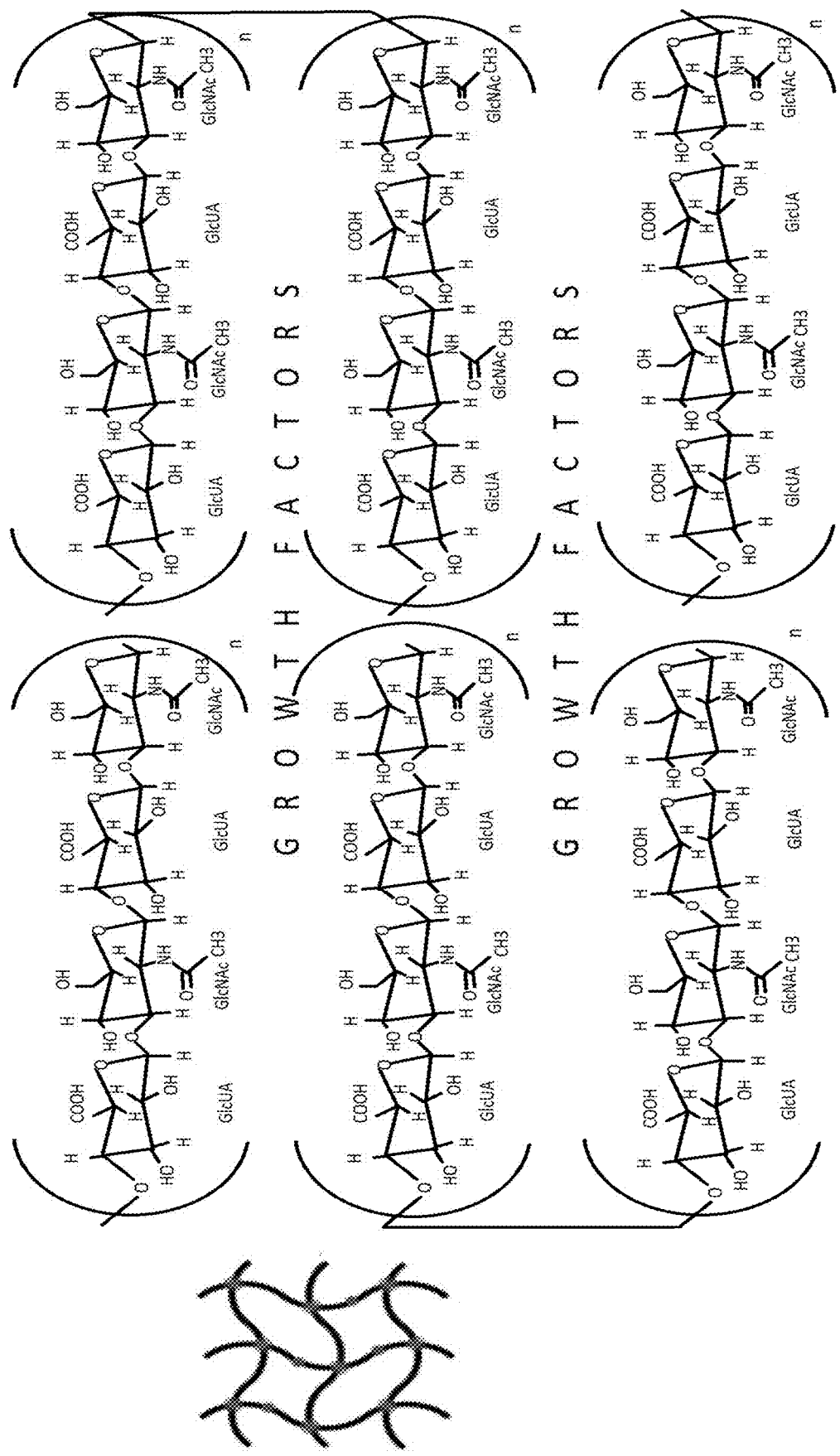
FIG. 1 shows different illustrations of hyaluronic acid: A) crosslinked and B) high molecular weight.
Figure 2:
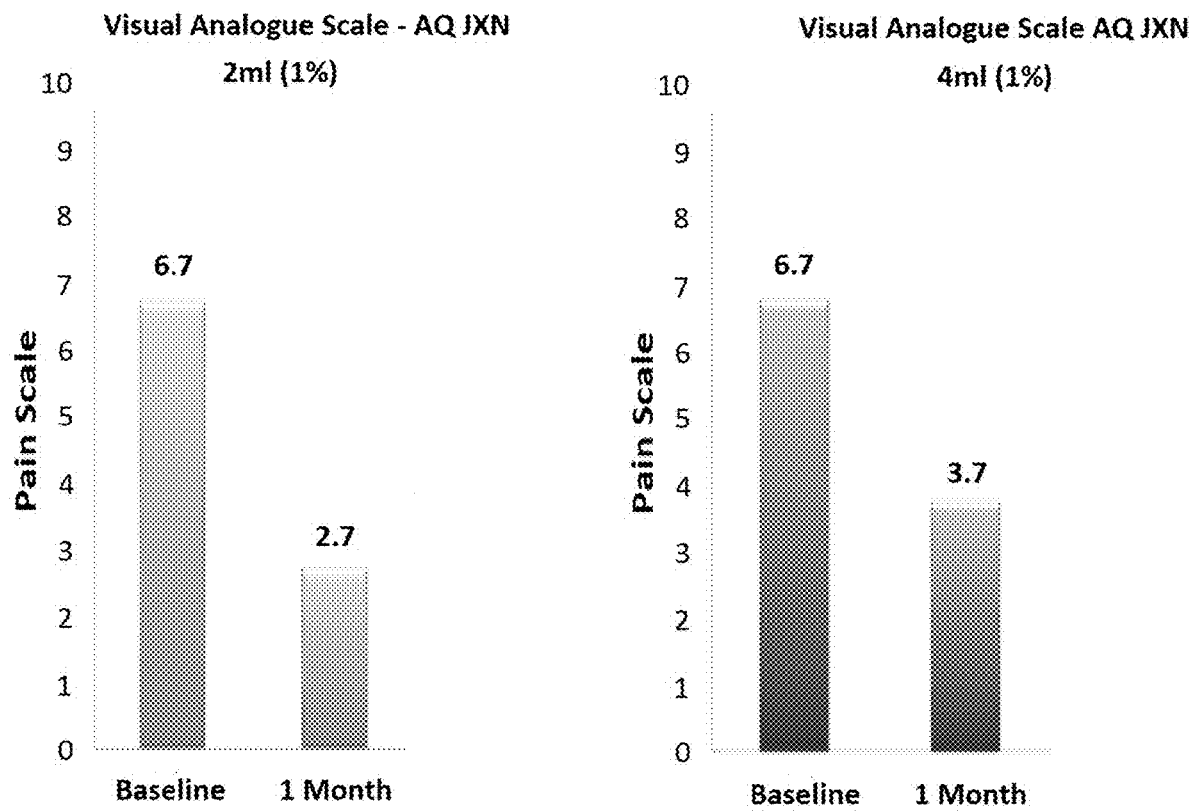
FIG. 2 shows a graph for Visual Analogue Scale for subjects treated with A) AQ JNX 2 ml (1%) injection or B) AQ JNX 4 ml (1%) injection.
Figure 3:
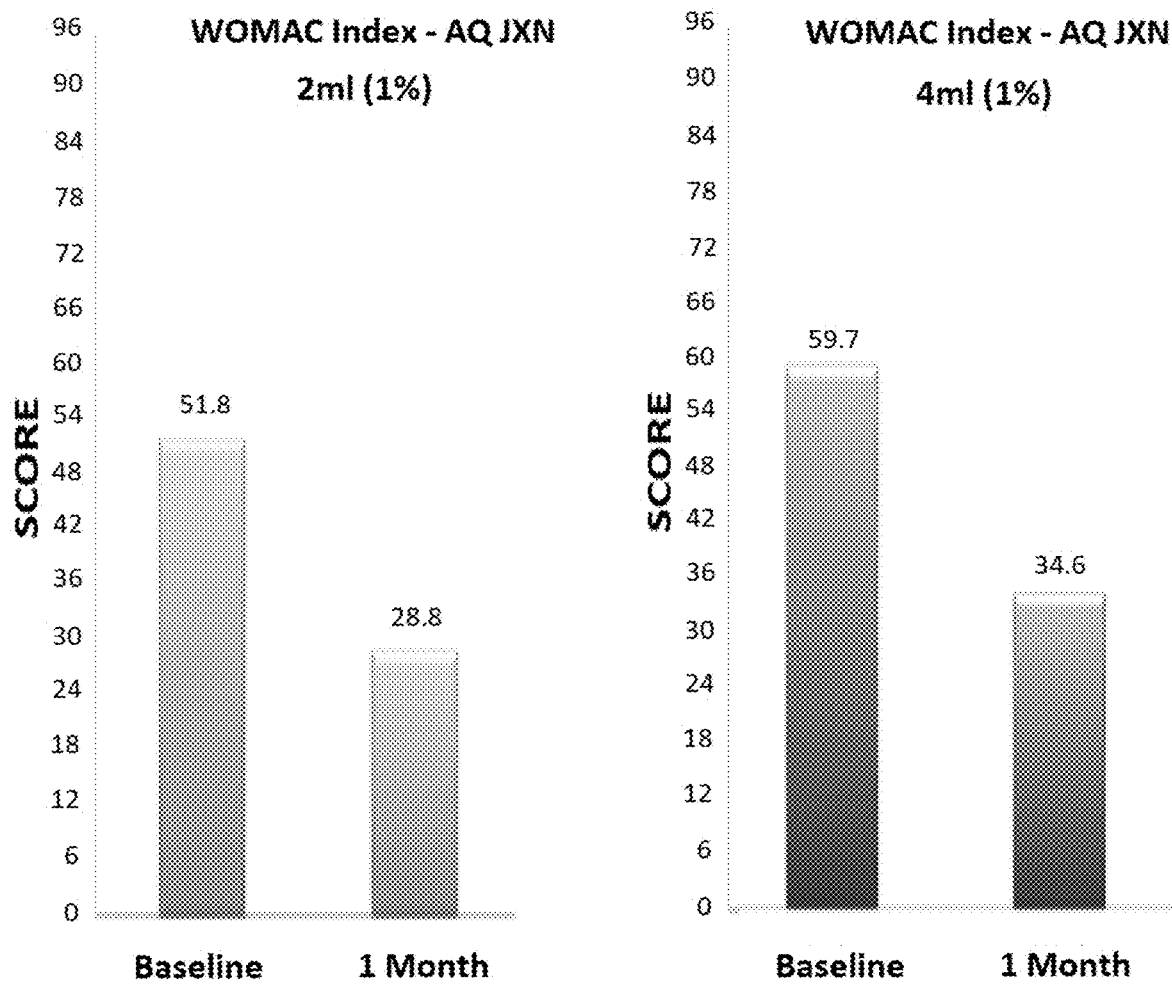
FIG. 3 shows a graph for WOMAC Index for subjects treated with A) AQ JNX 2 ml (1%) injection or B) AQ JNX 4 ml (1%) injection.
Figure 4:
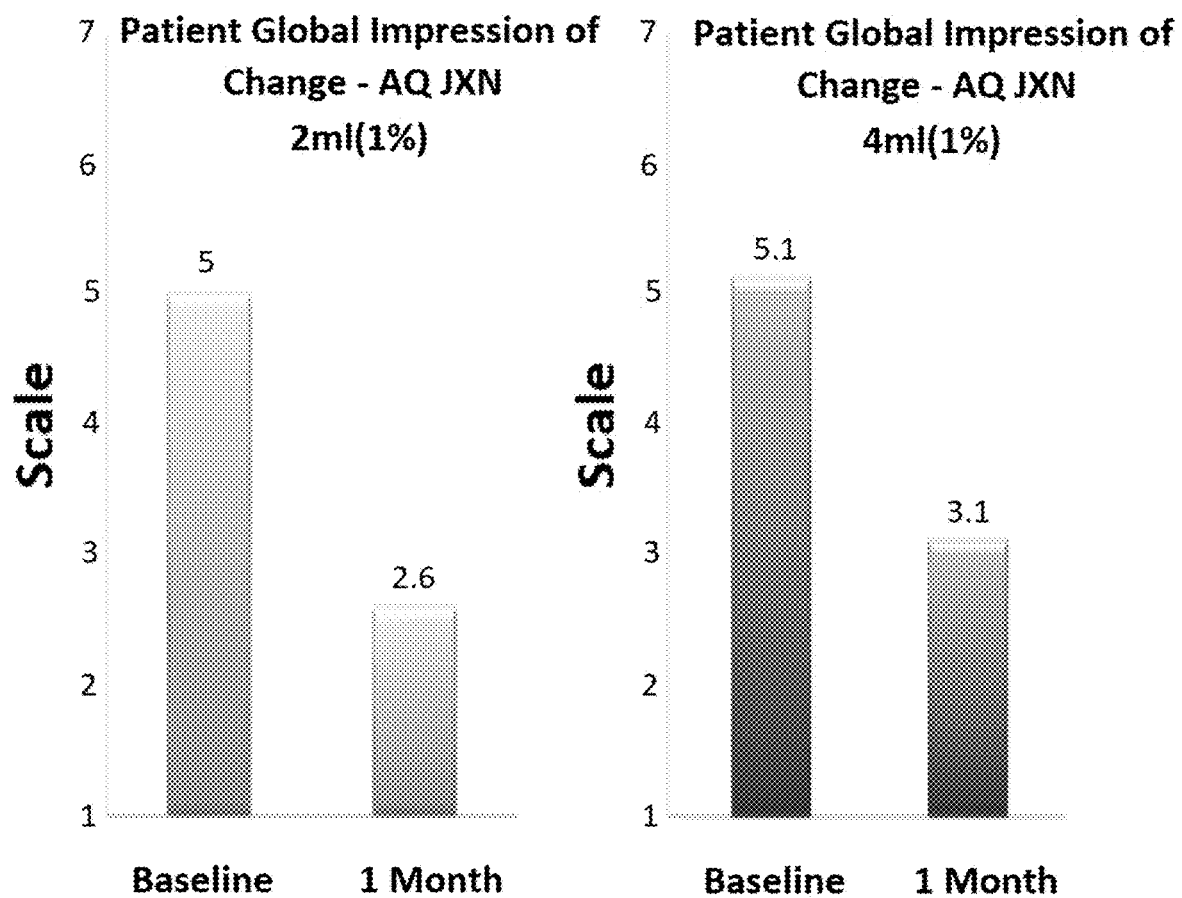
FIG. 4 shows a graph for Patient Global Impression of Change (PGIC) for subjects treated with A) AQ JNX 2 ml (1%) injection or B) AQ JNX 4 ml (1%) injection.
Figure 5:
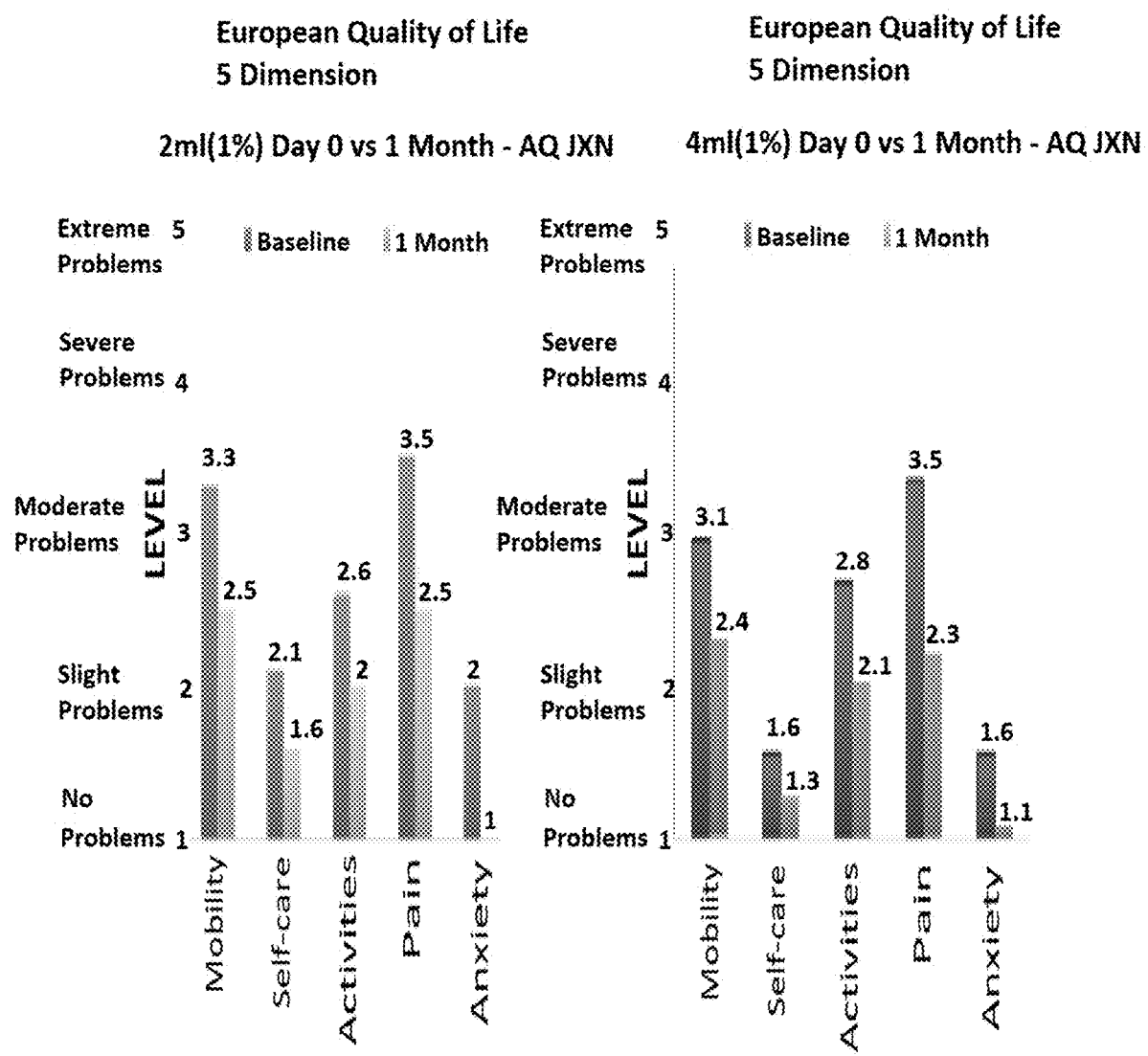
FIG. 5 shows a graph for European Quality of Life 5 Dimension for subjects treated with A) AQ JNX 2 ml (1%) injection or B) AQ JNX 4 ml (1%) injection.
Figure 6:
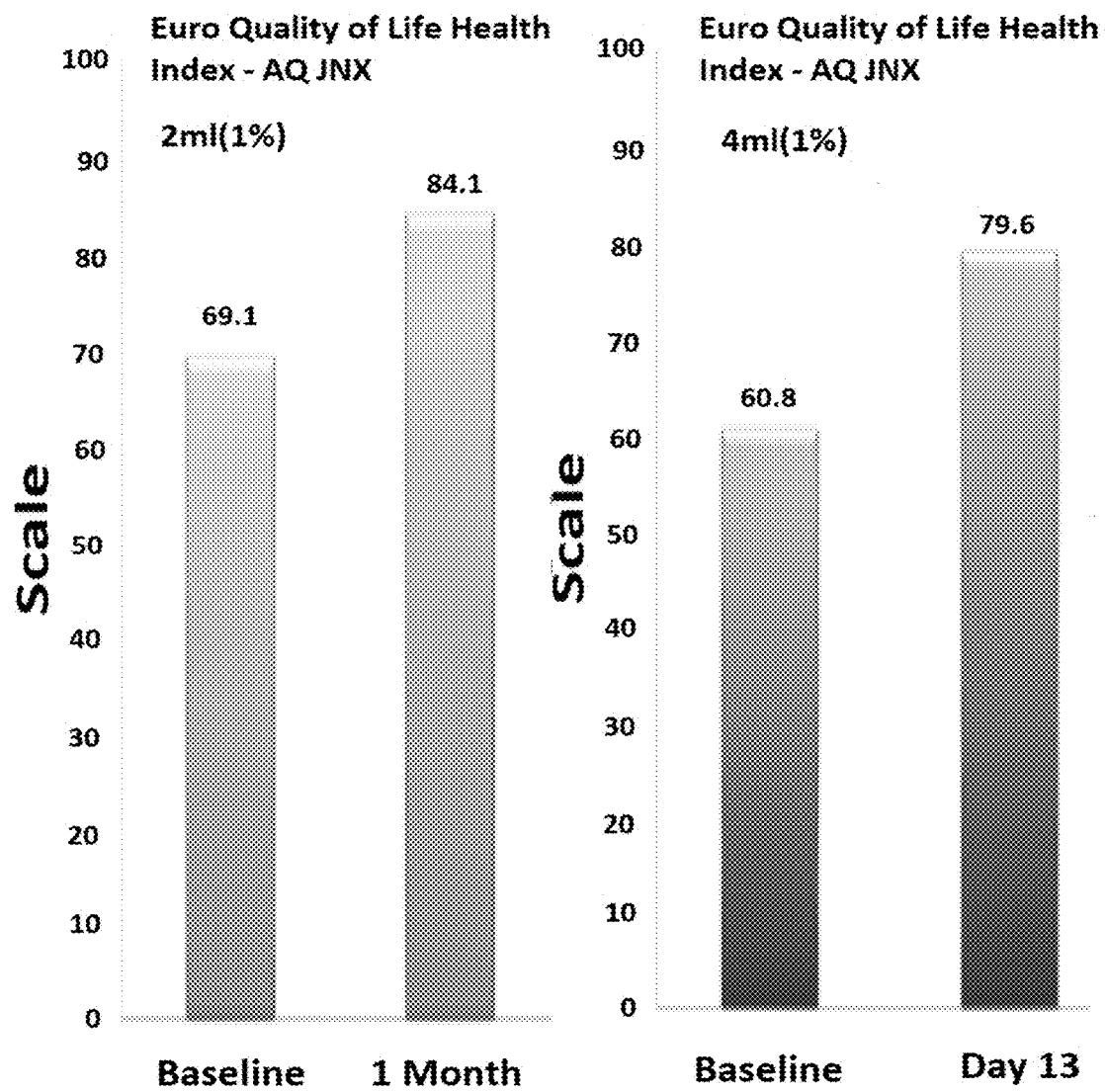
FIG. 6 shows a graph for Euro Quality of Life Index for subjects treated with A) AQ JNX 2 ml (1%) injection or B) AQ JNX 4 ml (1%) injection.
Figure 7:
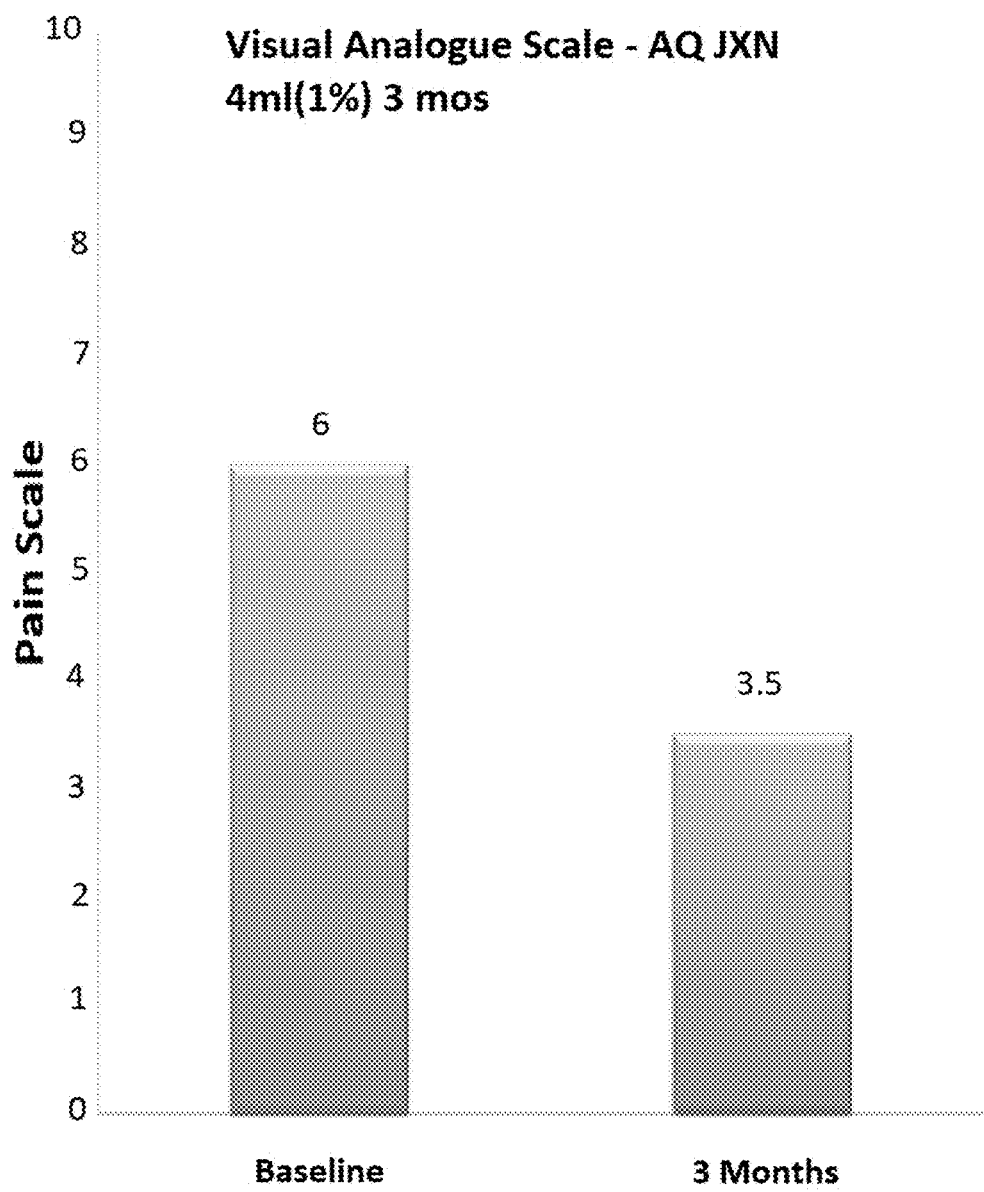
FIG. 7 shows a graph for Visual Analogue Scale for subjects treated with AQ JNX 4 ml (1%) injection (3 months).
Figure 8:
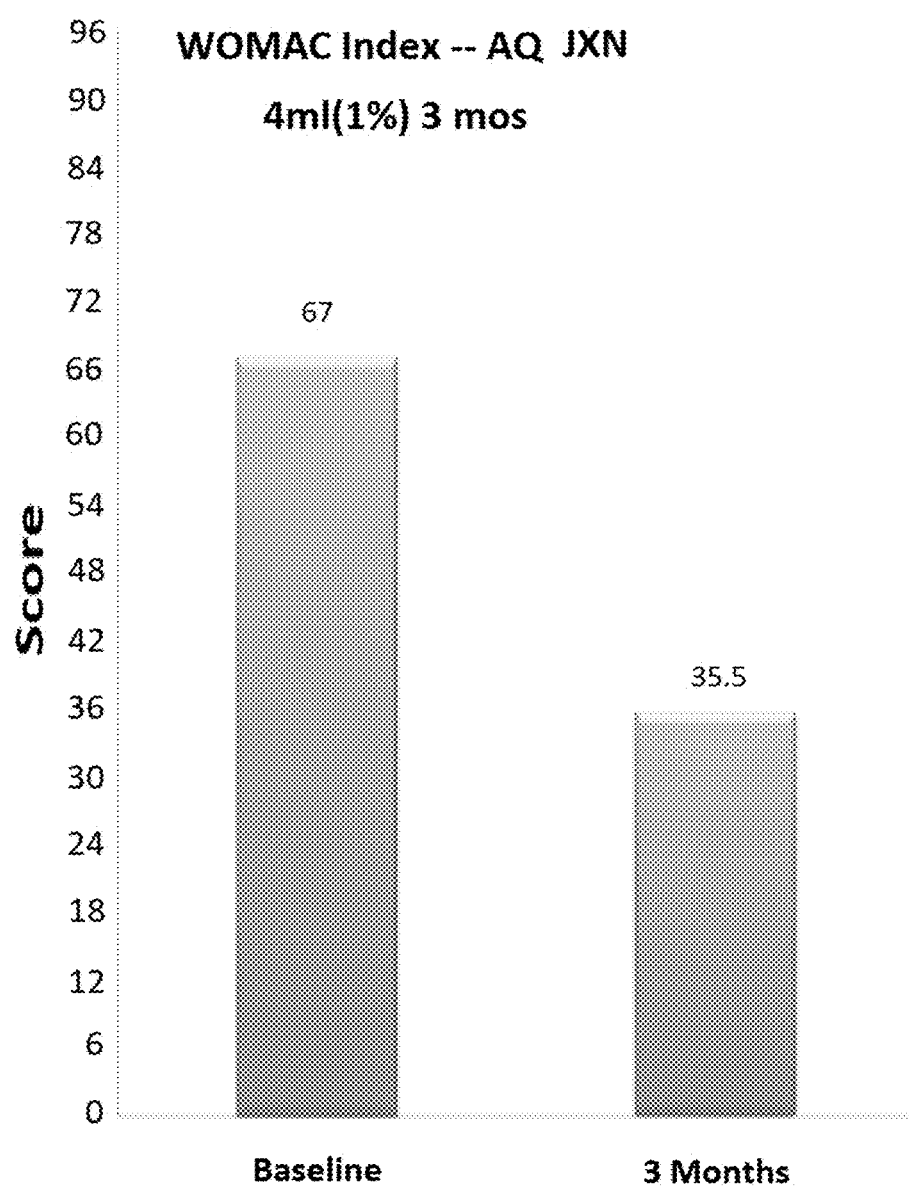
FIG. 8 shows a graph for WOMAC Index for subjects treated with AQ JNX 4 ml (1%) injection (3 months).
Figure 9:
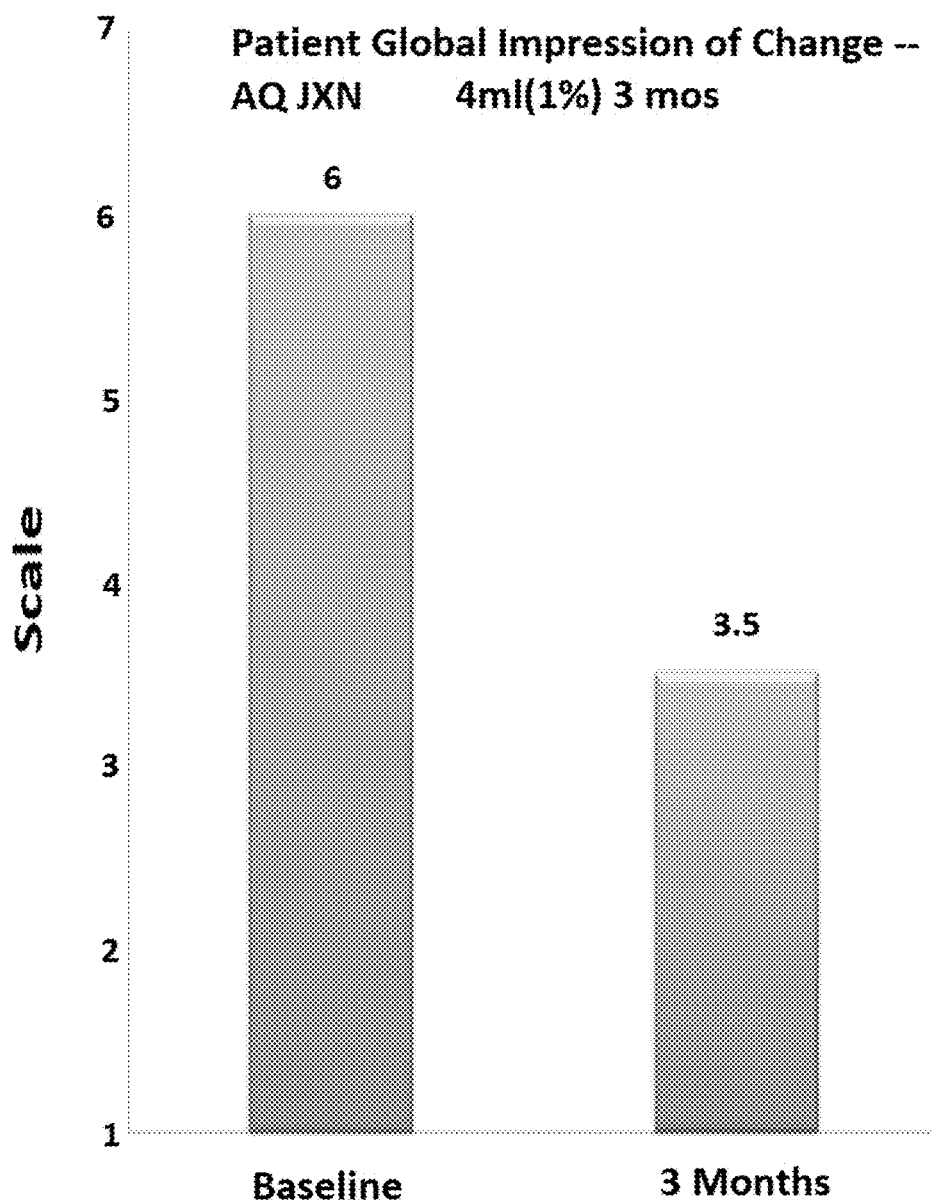
FIG. 9 shows a graph for Patient Global Impression of Change (PGIC) for subjects treated with AQ JNX 4 ml (1%) injection (3 months).
Figure 10:
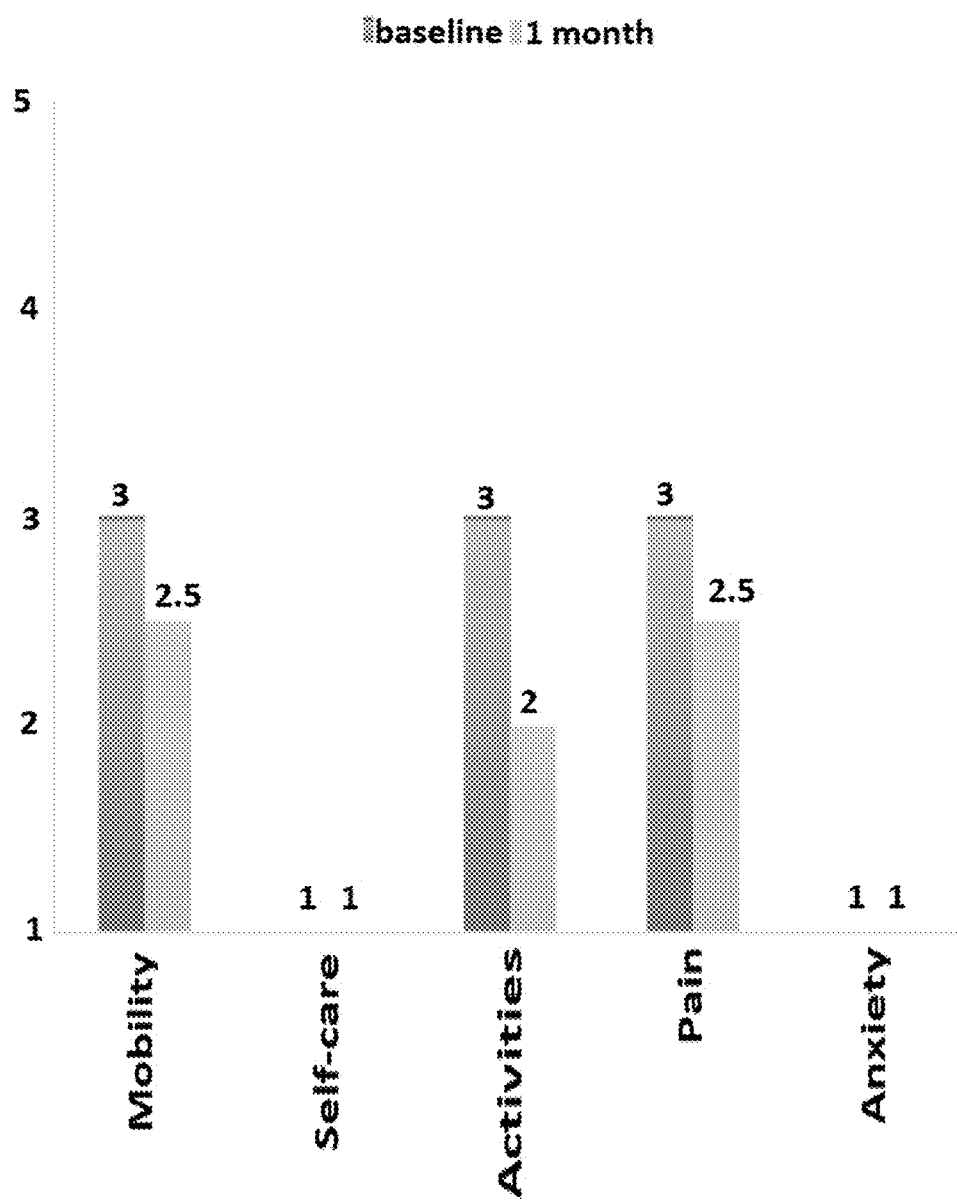
FIG. 10 shows a graph for European Quality of Life 5 Dimension for subjects treated with AQ JNX 4 ml (1%) injection (3 months).
Figure 11:
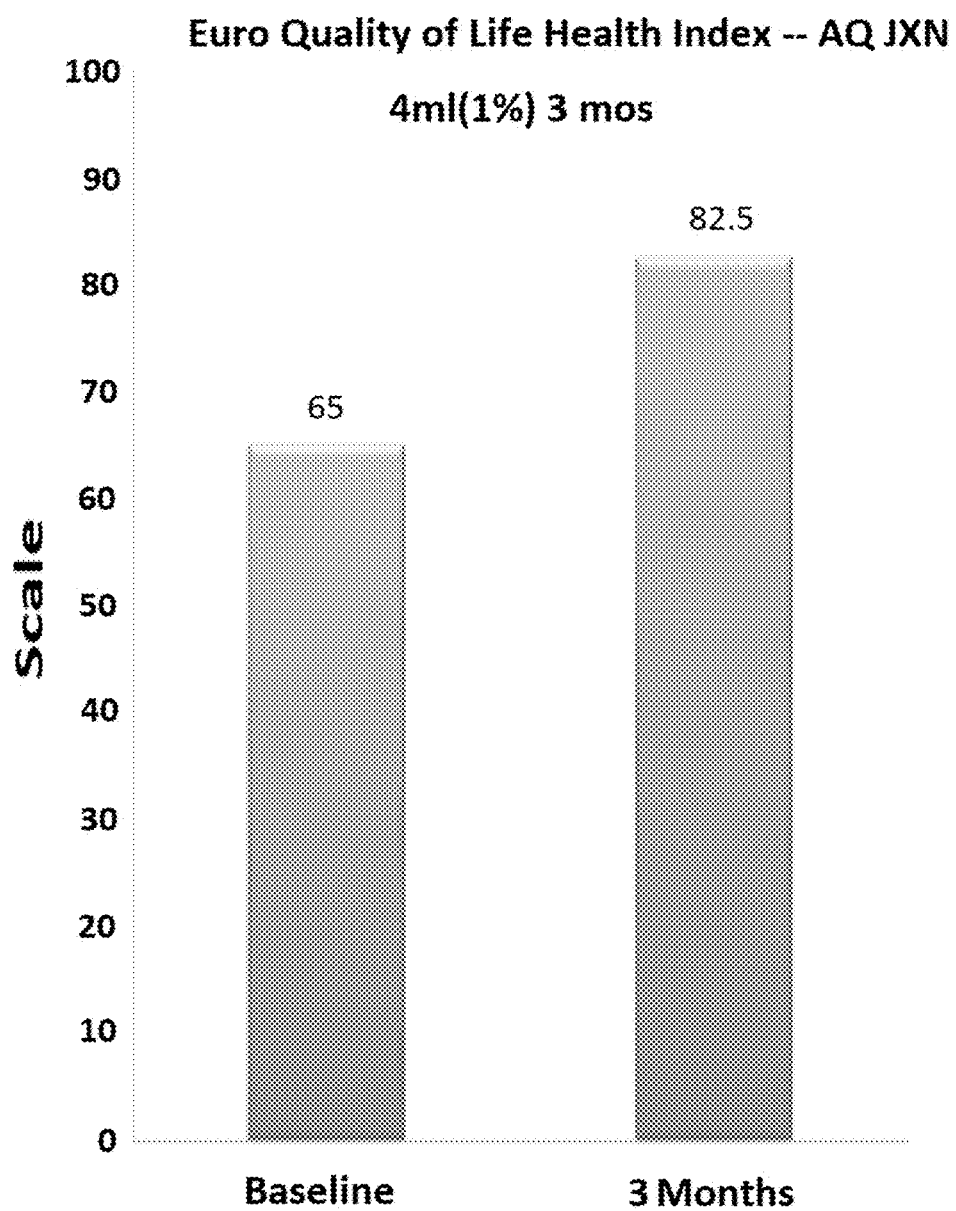
FIG. 11 shows a graph for Euro Quality of Life Index for subjects treated with AQ JNX 4 ml (1%) injection (3 months).

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a cell" includes one or more cells, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus <10% of particular term and "substantially" and "significantly" will mean plus or minus >10% of the particular term.

In some embodiments, the present invention relates to injectable therapeutic and/or prophylactic formulations for the joints in a subject, comprising hyaluronic acid and conditioned medium from two-dimensional cell cultures. The biologically active peptide and hyaluronic acid may be present in the form of a pharmaceutical acceptable salt.

The hyaluronic acid comprises high molecular weight hyaluronic acid. The cells may be cultured in monolayers on conventional substrates, roller bottles, beads, or any other two-dimensional culture systems, thereby providing at least some of the many known advantages of such scalable culture systems, including precise control of the cellular microenvironment. The cells are preferably human to reduce the risk of an immune response and include inter alia stromal cells, keratinocytes, melanocytes, parenchymal cells, mesenchymal stem cells, neural stem cells, pancreatic stem cells and/or embryonic stem cells. In some embodiments of the present invention, monolayer cultures of primary human foreskin fibroblasts are used to condition the nutrient medium in which they are bathed. Medium conditioned by such cell cultures contain a variety of naturally secreted proteins, including extracellular matrix proteins and biologically active growth factors.

Hyaluronic Acid (HA)

HA is a non-sulfated glycosaminoglycan found in the extra cellular matrix of most cells, and increased amounts are found in connective, neural and epithelial tissues. Hyaluronic acid is made up of linear polymeric chains in which disaccharide units of N-acetylglucosamine and glucoronic acid, bonded via by glucoside bonds, are repeated. It has been reported to have roles in promoting contact inhibition through binding to the cell surface glycoprotein CD44. HA is widely used in supporting joint function in arthritis patients (such as via knee injections), beauty products, and veterinary medicine (knee injections for race horses).

When cross-linked hyaluronic acid (FIG. 1A) breaks down, small fragments are created leading to further inflammation. As disclosed herein, the use of high molecular weight hyaluronic acid (FIG. 1B), which when broken down to creates longer chains of hyaluronic acid, and do not induce an inflammatory response. Further, layers produced by the high molecular weight hyaluronic acid create space for growth factors which factors contain anti-inflammatory cytokines that may regenerate cartilage (FIG. 1B).

Preferably the high molecular weight hyaluronic acid has a molecular weight greater than 300,000 Da, or greater than 800,000 Da.

The high molecular weight hyaluronic acid is present in the pharmaceutical composition at a concentration between 0.1 and 10% (w/w), most preferably between 0.5 and 2.5% (w/w).

The high molecular weight hyaluronic acid may be present in the form of a pharmaceutical acceptable salt.

Growth Factors and Osteoarthritis

Growth factors may be used as tools to enhance cartilage repair and conditioned media is rich in these factors. The growth factors are a diverse group of polypeptides that have important roles in the regulation of growth and tissue development, determining the behavior of all cells, including chondrocytes. An imbalance of regulatory factors, which may result from ageing, disease, or injury, may hinder tissue maintenance and repair, ultimately resulting in deleterious changes in gene expression, altered extracellular matrix, tissue degeneration and consequently an accelerated erosion of the articular surface, leading to end-stage arthritis.

The properties of conditioned media are based on the production and release of multiple growth and differentiation factors. Some of the basic cytokines identified in conditioned media that may be important to osteoarthritis treatment include, but are not limited to PDGF, TGF-β, FGF, and VEGF.

PDGF (Platelet-derived Growth Factor) appears to be the first growth factor present in a wound and initiates connective tissue healing through the promotion of collagen and protein synthesis. The primary effect of PDGF seems to be its mitogenic activity to mesoderm-derived cells such as fibroblasts, vascular muscle cells, glial cells and condrocytes. The most important specific activities of PDGF include angiogenesis and chemotaxis for fibroblasts and collagen synthesis.

TGF-β (Transforming Growth Factor β) superfamily are structurally related and only active as homo- or heterodimers linked together with a single disulfide bond. Activities include capacity to stimulate cartilage matrix synthesis, stimulation of extracellular matrix (ECM) synthesis, stimulation of chondrocyte synthetic activity, decreasing the catabolic activity of IL-1, stimulation of chondrogenesis of synovial lining and bone marrow-derived MSCs and enhanced repair of cartilage defects.

FGF is another family of factors which has been shown to have positive effect on cartilage repair.

VEGF (Vascular Endothelial Growth Factor) is the major regulator of vasculogenesis and angiogenesis and playing an important role in tissue regeneration.

Cell Cultures

The pre-conditioned cell culture medium may be any cell culture medium which adequately addresses the nutritional needs of the cells being cultured. Examples of cell media include, but are not limited to Dulbecco's Modified Eagle's Medium (DMEM), Ham's F12, RPMI 1640, Iscove's, McCoy's and other media formulations readily apparent to those skilled in the art, including those found in Methods For Preparation of Media, Supplements and Substrate For Serum-Free Animal Cell Culture Alan R. Liss, New York (1984) and Cell & Tissue Culture: Laboratory Procedures, John Wiley & Sons Ltd., Chichester, England 1996, both of which are incorporated by reference herein in their entirety. In one embodiment, DMEM without phenol red is used as the cell medium. The medium may be supplemented, with any components necessary to support the desired cell or tissue culture. In a related aspect, the medium is supplemented with Antibiotic-Antimycotic and L-glutamine. In one embodiment, the Antibiotic-Antimycotic and L-glutamine each constitute 1% of the medium, and the Antibiotic-Antimycotic comprises penicillin, streptomycin sulfate, and amphotericin B. Additionally serum, such as bovine serum, which is a complex solution of albumins, globulins, growth promoters and growth inhibitors may be added if desired. The serum should be pathogen free and carefully screened for mycoplasma bacterial, fungal, and viral contamination. Also, the serum should generally be obtained from the United States and not obtained from countries where indigenous livestock carry transmittable agents. Hormone addition into the medium may or may not be desired. In one embodiment, fetal bovine serum is added to the cell medium. In a related aspect, the fetal bovine serum constitutes about 5-20% of the medium.

The ingredients of pre-conditioned media may include amino-acids (both D and/or L-amino acids) such as glutamine, alanine, arginine, asparagine, cystine, glutamic acid, glycine, histidine, isoleucine, leucine, lysine, methionine, phenylalanine, proline, serine, threonine, tryptophan, tyrosine, and valine and their derivatives; acid soluble subgroups such as thiamine, ascorbic acid, ferric compounds, ferrous compounds, purines, glutathione and monobasic sodium phosphates.

Additional ingredients include sugars, deoxyribose, ribose, nucleosides, water soluble vitamins, riboflavin, salts, trace metals, lipids, acetate salts, phosphate salts, HEPES, phenol red, pyruvate salts and buffers (see, for example, Nouricel-MD available from Melbourne Dematology, Australia).

Other ingredients often used in media formulations include fat soluble vitamins (including A, D, E and K) steroids and their derivatives, cholesterol, fatty acids and lipids Tween 80, 2-mercaptoethanol pyramidines as well as a variety of supplements including serum (fetal, horse, calf, etc.), proteins (Insulin, transferrin, growth factors, hormones, etc.) antibiotics (gentamicin, penicillin, streptomycin, amphotericin B, etc.) whole egg ultra filtrate, and attachment factors (fibronectins, vitronectins, collagens, laminins, tenascins, etc.). In one embodiment, the amphotericin B used is Fungizone.

Of course, the media may or may not need to be supplemented with growth factors, peptides, and other proteins such as attachment factors since many of the cell constructs themselves elaborate such growth and attachment factors and other products into the media.

Other ingredients for the pre-conditioned culture medium, such as vitamins, growth and attachment factors, peptides, proteins and the like, can be selected by those of skill in the art in accordance with the particular need. Embodiments of the present invention may use any cell type appropriate to achieve the desired conditioned medium.

Genetically engineered cells may be used to condition the media. Such cells can be modified, for example, to express a desired protein or proteins so that the concentration of the expressed protein or proteins in the medium is optimized for the particular desired application. In accordance with aspects of the present invention, the cells and tissue cultures used to condition the medium may be engineered to express a target gene product which may impart a wide variety of functions, including but not limited to, improved properties in expressing proteins resembling physiological reactions, increased expression of a particular protein useful for a specific application, such as wound healing or inhibiting certain proteins such as proteases, lactic acid, and the like.

The medium may be conditioned by stromal cells, keratinocytes, melanocytes, parenchymal cells, mesenchymal stem cells (lineage committed or uncommitted progenitor cells), liver reserve cells, neural stem cells, pancreatic stem cells, and/or embryonic stem cells. The cells may include, but are not limited to, bone marrow, skin, liver, pancreas, kidney, neurological tissue, adrenal gland, mucosal epithelium, and smooth muscle, to name but a few. The fibroblasts and fibroblast-like cells and other cells and/or elements that comprise the stroma may be fetal or adult in origin, and may be derived from convenient sources such as skin, liver, pancreas, mucosa, arteries, veins, umbilical cord, and placental tissues, and the like. Such tissues and/or organs can be obtained by appropriate biopsy or upon autopsy. In fact, cadaver organs may be used to provide a generous supply of stromal cells and elements.

Fibroblasts may be readily isolated by disaggregating an appropriate organ or tissue which is to serve as the source of the fibroblasts. This may be accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase, and the like. Mechanical disruption can also be accomplished by a number of methods including, but not limited to, the use of grinders, blenders, sieves, homogenizers, pressure cells, or insonators to name but a few. For a review of tissue disaggregation techniques, see Freshney, Culture of Animal Cells: A Manual of Basic Technique, 2d Ed., A. R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, Culture of Animal Cells: A Manual of Basic Techniques, 2d Ed., A. R. Liss, Inc., New York, 1987, Ch. 11 and 12, pp. 137-168.

The isolation of fibroblasts may, for example, be carried out as follows: fresh tissue samples (e.g., human foreskin) are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency. In one aspect, deposit of viable human fibroblast cells designated AQHFF-0 has been made with the American Type Culture Collection ("ATCC"), 10801 University Blvd., Manassas, Va. on Feb. 14, 2011, having ATCC Accession No. PTA-11681.

In another aspect, the fibroblast cells are transformed with SV40 Large T antigen to establish long term immortalized cultures. In a related aspect, deposit of viable transformed human fibroblast cells designated AQHFF-SV40 has been made with the American Type Culture Collection ("ATCC"), 10801 University Blvd., Manassas, Va. on Feb. 14, 2011, having ATCC Accession No. PTA-11680.

The deposits were made in accordance with the terms and provisions of the Budapest Treaty. All restrictions on the availability to the public of the materials so deposited will be irrevocably removed upon the granting of the patent. The cells will be maintained for a term of at least thirty (30) years and at least five (5) years after the most recent request for the furnishing of a sample of the deposit is received by the depository, and at least beyond the enforceable life of the patent(s) for which the deposit was made, whichever is longer.

Embryonic stem cells and/or other elements that comprise the stroma may be isolated using methods known in the art. For instance, human embryonic stem cell populations and methods for isolating and using these cells have been reported in Keller et al., Nature Med., 5:151-152 (1999), Smith Curr. Biol. 8:R802-804 (1998); isolated from primordial germ cells, Shamblatt et al., PNAS 95:13726-1373 (1998); isolated from blastocytes, Thomason et al., Science 282:1145-1147 (1988). The isolation and culture of mesenchymal stem cells are known in the art. See Mackay et al., Tissue Eng. 4:415-428 (1988); William et al., Am Surg. 65:22-26 (1999). Likewise, neural stem cells may be isolated in the manner described in Flax et al., Nature Biotechnol., 16:1033-1039 (1998); and Frisen et al., Cell. Mol. Life Sci., 54:935-945 (1998).

The cells can be cultured in accordance with disclosed embodiments by any means known in the art, including in monolayer and beads and by any means (i.e., culture dish, roller bottle, a continuous flow system, etc.). In one aspect, the cells are cultured in an environment which enables aseptic processing and handling. Conventional means of cell and tissue culture have been limited by the need for human supervision and control of the media. This limits the amount of cells and tissue that can be cultured at a single time and consequently the volume of conditioned cell media that can be obtained at a single time. For this reason, the media may be conditioned in a manner allowing for large scale growth (yielding large scale conditioned media). In another aspect, cells may be arrested in growth phase by irradiation or mytomycin-c treatment to reduce the need for human supervision.

In some embodiments, the cells to be cultured may be first plated on dishes, then on flasks, then on two-liter roller bottle systems. Once a sufficient number of cells has been grown, the cells may be passaged to two-dimensional flat hexagonal shaped polysterene microcarriers. In one embodiment, the polystyrene microcarriers are Nunc 2D MicroHex carriers. In one aspect, microcarriers, with attached cells, may be suspended in ten-liter capacity bioreactors, which consist of a disposable sterile plastic bag placed on top of a rocker system. Each bag is expected to generate media for approximately 3 months before the cells are spent. When the media is subsequently collected, it may be filtered to remove any cells that may be present. The media may also be concentrated or diluted with PBS or $dH_2O$ to modify the growth factor concentrations. Corning 75 $cm^2$ tissue culture flasks may be used. Batches may be tested for growth factor/cytokine content through Upstate Labs Beadlyte Human Cytokine Profiler testing services using Luminex technology.

See also "What is preferred method for cell culture?": The Wave Bioreactor (System 20/50, Wave Biotech, New Jersey) in which cell culture (0.1-25 L volume) may be performed in pre-sterile, single use plastic bags. The bag may be filled with media, cells, and Nunc microcarriers and inflated to form a rigid gas-impermeable chamber. It may then placed on a rocking platform and rocked to induced waves. The gentle wave motion provides oxygenation and mixing of the media with minimal shear force.

The culturing of cells may be done on a laboratory scale or an industrial pilot or production scale. Scale up may be accomplished using commercially available products and technologies, e.g., Nunc Brand Products, including, Nunclon™ A surface across the range (from small single well to the Cell Factory 40 (CF40). Harvesting and clean up of secreted products may take place using conventional techniques.

In addition to the broad range of available surfaces and surface area configurations, particles may also be used in fermenters that support the growth of cells in stirred suspensions. Two-dimensional microcarriers (e.g., MICROHEX™ from Nunc) are hexagonal two-dimensional low-density particles requiring minimal stirring and therefore subjecting cells to minimal stress.

Traditional barriers to large-scale mammalian culture have now been addressed, with stirred-tank reactors emerging as one of industry's technology of choice. The issues of adapting cells to suspension culture, shear sensitivity and oxygen supply have been largely resolved. But for many low-volume and specialty applications, reactor technology remains diversified, with reactor types ranging from roller bottles to stacked plates and hollow fibers.

In general, where cell lines, as opposed to primary cultures, are utilized, they are preferably screened for human and animal pathogens. Depending upon the application, such screening may be more or less important, e.g., in wound healing or food additive applications, where pathogen free cells are desirable. Methods of screening for pathogens are well known in the art. The cell type will affect the properties of the conditioned medium.

A few researchers have explored the use of natural substrates related to basement membrane components. Basement membranes comprise a mixture of glycoprotein and proteoglycans that surround most cells in vivo. For example, Reid and Rojkund, 1979, In, Methods in Enzymology, Vol. 57, Cell Culture, Jakoby & Pasten, eds., New York, Acad. Press, pp. 263-278; Vlodaysky et al., 1980, Cell 19:607-617; Yang et al., 1979, Proc. Natl. Acad. Sci. USA 76:3401 have used collagen for culturing hepatocytes, epithelial cells and endothelial tissue. Growth of cells on floating collagen (Michalopoulos and Pitot, 1975, Fed. Proc. 34:826) and cellulose nitrate membranes (Savage and Bonney, 1978, Exp. Cell Res. 114:307-315) have been used in attempts to promote terminal differentiation.

Cultures of mouse embryo fibroblasts have been used to enhance growth of cells, particularly at low densities. This effect is thought to be due partly to supplementation of the medium but may also be due to conditioning of the substrate by cell products. In these systems, feeder layers of fibroblasts are grown as confluent monolayers which make the surface suitable for attachment of other cells. For example, the growth of glioma on confluent feeder layers of normal fetal intestine has been reported (Lindsay, 1979, Nature 228:80).

Stromal cells may be genetically engineered to adjust the level of protein products secreted into the culture medium to improve the concentration of recovered product obtained from the conditioned medium. For example, anti-inflammatory factors, e.g., anti-GM-CSF, anti-TNF, anti-IL-1, anti-IL-2, and the like. Alternatively, stromal cells may be genetically engineered to "knock out" expression of native gene products that promote inflammation, e.g., GM-CSF, TNF, IL-1, IL-2, or "knock out" expression of MHC in order to lower the risk of rejection. The cells used to condition the medium may be genetically modified to alter the concentration of proteins found in the medium. The conditioned cell medium is processed for uses which include cosmetic additives and any pharmaceutical applications related to topical formulations for treatment and/or prevention of aging, wrinkles, and wound healing. In one embodiment, compositions and methods are disclosed for stimulating hair growth, including stimulation of hair growth on the head and eyelashes. In some embodiments, the invention also relates to compositions containing extracellular matrix proteins and/or other purified protein(s) derived from the conditioned medium.

The cells may be engineered to express a target gene product which is biologically active and provides a chosen biological function, which acts as a reporter of a chosen physiological condition, which augments deficient or defective expression of a gene product, or which provides antiviral, anti-bacterial, anti-microbial, or anti-cancer activity. In accordance with the present invention, the target gene product may be a peptide or protein, such as an enzyme, hormone, cytokine, antigen, or antibody, a regulatory protein, such as a transcription factor or DNA binding protein, a structural protein, such as a cell surface protein, or the target gene product may be a nucleic acid such as a ribosome or antisense molecule. The target gene products include, but are not limited to, gene products which enhance cell growth. For example, the genetic modification may up-regulate an endogenous protein, introduce a new protein or regulate ion concentration by expressing a heterologous ion channel or altering endogenous ion channel function. Examples include, but are not limited to engineered tissues that express gene products which are delivered systemically (e.g., secreted gene products such as proteins including growth factors, hormones, Factor VIII, Factor IX, neurotransmitters, and enkaphalins).

Methods for preparing DNA constructs containing the gene of interest, for transforming or transfecting cells, and for selecting cells carrying and expressing the gene of interest are well-known in the art. See, for example, the techniques described in Maniatis et al., 1989, Molecular Cloning, A Laboratory Manual, Cold Spring Harbor Laboratory Press, Cold Spring Harbor, N.Y.; Ausubel et al., 1989, Current Protocols in Molecular Biology, Greene Publishing Associates & Wiley Interscience, N.Y.; and Sambrook et al., 1989, Molecular Cloning: A Laboratory Manual, 2nd Ed., Cold Spring Harbor Laboratory Press, Cold Spring Harbor, N.Y.

The cells can be engineered using any of a variety of vectors including, but not limited to, integrating viral vectors, e.g., retrovirus vector or adeno-associated viral vectors; or non-integrating replicating vectors, e.g., papilloma virus vectors, HSV vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter. Other methods of introducing DNA into cells include the use of liposomes, lipofection, electroporation, a particle gun, or by direct DNA injection. In one aspect of the present invention, the cells are transformed with an SV40 Large T Antigen containing vector to establish immortalized cells. In a related aspect, the vector is an SV40 Large T (SVLT) antigen mammalian expression vector, where such a vector contains and proximal SVLT promoter and distal SVLT element which flank the SV Large T antigen encoding sequence, one or more bacteriophage promoters, one or more multiple cloning sites, one or more bacterial cell selection genes, one or more mammalian cell selection genes, one or more sites for integration into a mammalian host, or one or more elements for plasmid propagation/replication in bacterial hosts, or a combination thereof. For example, the vector may be pBsSVD2005 (AddGene, Cambridge Mass.). See, e.g., FIG. 1.

The cells are preferably transformed or transfected with a nucleic acid, e.g., DNA, controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, may be cloned and expanded into cell lines. This method may be advantageously used to engineer cell lines which express the gene product into the media.

Any promoter may be used to drive the expression of the inserted gene. For example, viral promoters include but are not limited to the CMV promoter/enhancer, SV40, papillomavirus, Epstein-Barr virus, elastin gene promoter and B-globin. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters may be used to drive the expression of the inserted gene when necessary. Inducible promoters may be built into integrating and/or replicating vectors. For example, inducible promoters include, but are not limited to, metallothionein and heat shock protein.

According to one embodiment, the inducible promoters used for expressing exogenous genes of interest are those that are the native promoters of those regulatory proteins as disclosed herein that are induced as a result of cyropreservation and subsequent thawing. For example, the promoter of TGF-B, VEGF, or various known heat shock proteins may be used as the expression control element, i.e., may be operatively linked to an exogenous gene of interest in order to express a desired gene product in the tissue constructs conditioning the cell media.

A variety of methods may be used to obtain the constitutive or transient expression of gene products engineered into the cells. For example, the transkaryotic implantation technique described by Seldon et al., 1987, Science 236: 714-718 may be used. "Transkaryotic", as used herein, suggests that the nuclei of the implanted cells have been altered by the addition of DNA sequences by stable or transient transfection. In one aspect, the cells may be engineered to express such gene products transiently and/or under inducible control during the post-operative recovery period, or as a chimeric fusion protein anchored to the stromal cells, for example, as a chimeric molecule composed of an intracellular and/or transmembrane domain of a receptor or receptor-like molecule, used to the gene product as the extracellular domain.

In other aspects of the present invention, the two-dimensional tissue cultures which condition the cell media may contain fibroblasts, keratinocytes, melanocytes, mesenchymal stem cells, liver reserve cells, neural stem cells, pancreatic stem cells, and/or embryonic stem cells and/or parenchymal cells and/or parenchymal stem cells found in many tissue types, including but not limited to bone marrow, skin, liver, pancreas, kidney, adrenal and neurologic tissue, as well as tissues of the gastrointestinal and genitourinary tracts, and the circulatory system. See e.g., U.S. Pat. Nos. 4,721,096; 4,963,489; 5,032,508; 5,266,480; 5,160,490; and 5,559,022, each of which is incorporated by reference herein in its entirety.

In other embodiments, different cell types may be cultured separately, wherein conditioned medium enriched with different cell type-specific factors may be formulated by mixing desired proportions of media conditioned by these different cell types. Such individual two-dimensional culturing may employ any of the above-mentioned cell types including genetically engineered cells and cell lines.

Conditioned Medium

Applicants provide methods to deliver critical structural proteins and relevant growth factors directly to the joint. This may be accomplished by combining growth factor-enriched conditioned medium from one or more cell types grown independently under highly controlled monolayer (two-dimensional) culture conditions, with a formulated hyaluronic preparation.

In one embodiment, the homogeneous growth factor-enriched conditioned medium from a single cell type is employed in the joint formulation. In other variations, the conditioned media from different cell types are mixed to provide optimal growth factor and secreted structural protein constituents.

Concentration may be accomplished by any conventional methods known in the art, including for example, freeze-drying, vacuum-drying, evaporation, and the like. Moreover, particular growth factors may be concentrated by affinity chromatography or other conventional methods for protein/peptide purification. Dilution methods may include addition of deionized water. Preservation methods may include inter alia, freeze-drying, spray-drying, foam-drying, and the like. In one embodiment, the medium is filtered with a 7 micron filter, then preservatives and other ingredients and/or supplements are added to the medium, and the medium is stored in a refrigerator. In addition, the conditioned medium may be subjected to further processing, e.g., affinity chromatography, to differentially concentrate or remove certain medium components, as detailed below.

Following removal of the cell conditioned medium, it may be necessary to further process the resulting supernatant. Such processing may include, but is not limited to, centrifugation, product isolation and purification, dilution of the media or concentration of the media by a water flux filtration device or by defiltration using the methods described in Cell & Tissue Culture: Laboratory Procedures, supra, pp 29 D:0.1-29D:0.4.

The conditioned medium may be further processed for product isolation and purification to remove unwanted proteases, for example. The methods used for product isolation and purification so that optimal biological activity is maintained will be readily apparent to one of ordinary skill in the art. For example, it may be desirous to purify a growth factor, regulatory factor, peptide hormone, antibody, or the like. Such methods include, but are not limited to, gel chromatography (using matrices such as Sephadex) ion exchange, metal chelate affinity chromatography with an insoluble matrix such as cross-linked agarose, HPLC purification and hydrophobic interaction chromatography of the conditioned media. Such techniques are described in greater detail in Cell & Tissue Culture; Laboratory Procedures, supra. Of course, depending upon the desired application of the conditioned medium, and/or products derived thereof, appropriate measures must be taken to maintain sterility. Alternatively, sterilization may be necessary and can be accomplished by methods known to one of ordinary skill in the art, such as, for example, heat and/or filter sterilization taking care to preserve the desired biological activity.

In one embodiment, the media is filtered or centrifuged to prevent cell inclusion. It may then be diluted, e.g., with PBS or deionized water, if the growth factor concentrations are too high. Alternatively, the conditioned medium may be concentrated if the growth factor levels are not sufficiently high. The diluted or concentrated media may then be combined with the cream/gel formulation.

As previously mentioned, the conditioned medium contains numerous products which may be concentrated. For example, human dermal fibroblasts synthesize and secrete collagen precursors and a fraction of these precursors are incorporated into the extracellular matrix. This incorporation requires the removal of terminal peptides (N- and C-peptides) which significantly lowers the solubility of the collagen molecules (the rest of the secreted collagen remains in solution due to lack of proteolysis). Generally, soluble collagen may be obtained under neutral pH conditions at high salt concentrations. See Kielty, C. M., I. Hopkinson, et al. (1993), Collagen: The Collagen Family: Structure, Assembly, and Organization in the Extracellular Matrix, Connective Tissue and Its Heritable Disorders: molecular, genetic and medical aspects. P. M. Royce and B. Steinmann. New York, Wiley-Liss, Inc.: 103-149).

It should be understood that the following protocol is offered by way of example and may be modified using methods known to those of skill in the relevant art: To purify the collagen, add 240 ml of medium conditioned with fibroblasts to 240 ml 5M NaCl (a 1:1 ratio of medium to salt) and precipitate for 16 hours at 4° C. Centrifuge the suspension for approximately 20 minutes at 4000×g. Discard the supernatant. Wash the pellet with 10 ml of a solution of 50 mM Tris-HCl (pH 7.5) and 2.4M NaCl. Centrifuge for 20 minutes at 4000×g and discard the supernatant. Resuspend the pellet in 10 ml of 0.5M acetic acid. To remove the propeptides, add 0.1 ml of pepsin (100 mg/mL) (Sigma Chemical, St. Louis, Mo.) and digest for 16 hours at 4° C. (this removes the propeptides but leaves the triple helix intact). Centrifuge the suspension for 20 minutes at 4000×g. Recover supernatant and discard the pellet. Add 2.1 ml of 5M NaCl and 0.5M acetic acid to a final volume of 15 ml (final NaCl concentration of 0.7M). Precipitate for approximately 16 hours at 4° C. Centrifuge the suspension for 20 minutes at 4000×g and discard the supernatant. Dissolve pellet in 0.5 ml of 0.5M acetic acid solution. The purity of the collagen should be at least 90% and may be analyzed by standard methods known in the art such as SDS-PAGE, for example.

The conditioned medium compositions may be comprised of any known defined or undefined medium and may be conditioned using any eukaryotic cell type. The medium may be conditioned by stromal cells, keratinocytes, melanocytes, parenchymal cells, mesenchymal stem cells, liver reserve cells, neural stem cells, pancreatic stem cells, and/or embryonic stem cells. The cell type will affect the properties of the conditioned medium. For example, a medium conditioned with astrocytes and neuronal cells will elaborate certain characteristic metabolites and proteins so that such a conditioned medium is preferred for certain nerve repair applications. The cell culture may further be cultured with parenchymal cells such as the cells of the skin, bone, liver, nerve, pancreas, etc., resulting in a conditioned medium containing characteristic extracellular proteins and other metabolites of that tissue type. Accordingly, in accordance with one embodiment of the present invention, media conditioned by different cell types may be mixed in different proportions to provide a formulation adapted to deliver a combination of cell or tissue-specific conditioning characteristics.

Additionally, each cell type may also be genetically modified as detailed above. The genetic modification may be used to alter the concentration of one or more component in the medium such as, for example, to upregulate a protein, to introduce a new protein, or to regulate ion concentration. Further, cells including heterogeneous primary cell cultures and/or cell lines may be cloned, mutated, and/or selected for desired phenotype, genotype, responsiveness to culture conditions (e.g., temperature, pH, pharmacologic agents, etc.), protein secretory characteristics, and the like.

Commercial Applications

In certain embodiments, hyaluronic acid combined with growth factor-enriched conditioned medium may be used in the form of injectables. Indeed, the growth factor-enriched conditioned medium may be used in combination with other injectable agents to provide enhanced treatment of inflamed joints.

In one aspect, a combination of the hyaluronic acid and conditioned media includes TGF Beta-1, TGF Beta-2, TGF Beta-3, IL-3, IL-6, IL-7, and IL-8, where the conditioned media is present at a concentration of at least 20% (wt %). In a related aspect, the combination includes about 1-3 ng/mL TGF Beta-1, about 100-160 pg/mL TGF Beta-2, about 50-100 pg/mL TGF Beta-3, about 60 pg/mL IL-3, about 11 pg/mL IL6, about 50 pg/ML IL-7, and about 4-10 pg/mL IL-8, and where the conditioned media is present at about 30-42% (wt %).

The hyaluronic acid/conditioned medium may be combined with other active agents such as antibiotics and analgesics.

Modified hyaluronic acid derivatives may also be useful. As used herein, the term "hyaluronic acids" refers to natural and chemically modified hyaluronic acids. Modified hyaluronic acids may be designed and synthesized with preselected chemical modifications to adjust the rate and degree of cross-linking and biodegradation.

In embodiments, the hyaluronic acid/medium combination may be formulated with a pharmaceutically acceptable carrier as a vehicle for internal administration. Also, the medium may be further processed to concentrate or reduce one or more factor or component contained within the medium, for example, enrichment of a growth factor using immunoaffinity chromatography or, conversely, removal of a less desirable component, for any given application as described herein.

The hyaluronic acid/conditioned cell medium composition may also be added to devices used in periodontal surgery in order to promote uniform tissue repair, to provide bone grafts, to provide surgical space fillers, and to promote soft tissue augmentation.

In another embodiment, the compositions as disclosed herein may be lyophilized/freeze-dried or added to bone filling compositions to accelerate bone growth.

Other Active Agents

Also, products which may be added include, but are not limited to, antibiotics, antivirals, antifungals, steroids, analgesics, antitumor drugs, investigational drugs or any compounds which would result in a complimentary or synergistic combination with the factors in the conditioned media.

Pharmacologic agents may also be incorporated into preferred embodiments of the conditioned medium formulations, including for example, the addition of vitamins or minerals. For instance, those that function directly or indirectly through interactions or mechanisms involving amino acids, nucleic acids (DNA, RNA), proteins or peptides (e.g., RGD peptides), carbohydrate moieties, polysaccharides, liposomes, or other cellular components or organelles for instance receptors and ligands.

The following agents are believed to exert their actions extracellularly or at specific membrane receptor sites. These include corticoids and other ion channel blockers, growth factors, antibodies, receptor blockers, fusion toxins, extracellular matrix proteins, peptides, or other biomolecules (e.g., hormones, lipids, matrix metalloproteinases, and the like), radiation, anti-inflammatory agents including cytokines such as interleukin-1 (IL-1), and tumor necrosis factor alpha (TNF-a), gamma interferon (interferon-y), and Tranilast, which modulate the inflammatory response. Growth factor receptor agonists are also within the scope of possible active agents that may be admixed with the conditioned medium formulations.

Other groups of agents exert their effects at the plasma membrane. These include those involved in the signal transduction cascade, such as coupling proteins, membrane associated and cytoplasmic protein kinases and effectors, tyrosine kinases, growth factor receptors, and adhesion molecules (selectins and integrins).

Some compounds are active within the cytoplasm, including for example, heparin, ribozymes, cytoxins, antisense oligonucleotides, and expression vectors. Other therapeutic approaches are directed at the nucleus. These include gene integration, proto-oncogenes, particularly those important for cell division, nuclear proteins, cell cycle genes, and transcription factors.

Specific growth factors, interleukins and interferons that may be used in accordance with embodiments of the present invention include, but are not limited to:

Epidermal Growth Factor (EGF): promotes proliferation of mesenchymal, glial and epithelial cells;

Platelet-Derived Growth Factor (PDGF): promotes proliferation of connective tissue, glial and smooth muscle cells; and Fibroblast Growth Factors (FGFs): promotes proliferation of many cells; inhibits some stem cells; induces mesoderm to form in early embryos;

Transforming Growth Factors-ß (TGFs-ß):
Transforming Growth Factor-a-(TGF-α): may be important for normal wound healing;

Nerve Growth Factor (NGF): promotes neurite outgrowth and neural cell survival;

Erythropoietin (Epo): promotes proliferation and differentiation of erythrocytes;

Insulin-Like Growth Factor-I (IGF-I): promotes proliferation of many cell types; and Insulin-Like Growth Factor-II (IGF-II): promotes proliferation of many cell types primarily of fetal origin.

In some embodiments, the interleukins may be used to boost local immune function and/or modulate inflammatory responses. Some of the interleukins and their primary activity include, but are not limited to, the following:

IL1-α and β: co-stimulation of APCs and T cells, inflammation;

IL-2: proliferation of B cells and activated T cells, NK functions;

IL-3: growth of hematopoietic progenitor cells;

IL-4: B cell proliferation, eosinophil and mast cell growth and function, IgE and class II MHC expression on B cells, inhibition of monokine production;

IL-5: eosinophil growth and function;

IL-6: acute phase response, B cell proliferation, thrombopoiesis, synergistic with M-1 and TNF on T cells;

IL-7: T. and B lymphopoiesis;

IL-8: chemoattractant for neutrophils and T cells;

IL-9: hematopoietic and thymopoietic effects;

IL-10: inhibits cytokine production, promotes B cell proliferation and antibody production, suppresses cellular immunity, mast cell growth;

IL-11: synergistic hematopoietic and thrombopoietic effects;

IL-12: proliferation of NK cells, INF-γ production, promotes cell-mediated immune functions; and IL-13: IL-4-like activities.

In some embodiments, the interferons may be used to boost local immune function and/or modulate inflammatory responses. Some of the interferons and their primary activity include, but are not limited to, the following:

INF-α and -ß: antiviral effects, induction of class I MHC on all somatic cells, activation of NK cells and macrophages;

INF-γ: induces of class I MHC on all somatic cells, induces class II MHC on APCs and somatic cells, activates macrophages, neutrophils, NK cells, promotes cell-mediated immunity, antiviral effects;

Tumor Necrosis Factor-α (TNF-α): induces the expression of other autocrine growth factors, increases cellular responsiveness to growth factors and induces signaling pathways that lead to proliferation;

Tumor Necrosis Factor-ß (TNF-ß): (also called lymphotoxin) ability to kill a number of different cell types, as well as the ability to induce terminal differentiation in others. One significant non-proliferative response to TNF-ß is an inhibition of lipoprotein lipase present on the surface of vascular endothelial cells;

Colony Stimulating Factors (CSFs): stimulate the proliferation of specific pluripotent stem cells of the bone marrow in adults. Granulocyte-, Macrophage-CSFs. Epo and IL-3 are also considered a CSF.

Other peptides include copper peptides, EPO-derived peptide (see e.g. U.S. Pat. No. 9,765,128, herein incorporated by reference in its entirety), Sema 3A protein derivative (see, e.g., U.S. Pat. No. 9,637,519, herein incorporated by reference in its entirety) snake venom C-type lectin like proteins (CLPs; see, e.g., U.S. Pat. No. 9,605,038, herein incorporated by reference in its entirety), kappa opioid synthetic peptide (see, e.g., U.S. Pat. No. 9,321,810).

Therapeutic Formulations

The hyaluronic acid-conditioned medium composition may be formulated for preventing, reducing and/or joint pain and inflammation associated with osteoarthritis. As stated above, an imbalance of regulatory factors, may cause an accelerated erosion of the articular surface, leading to end-stage arthritis.

The conditioned medium contains growth factors and inflammatory mediators such as, for example, PDGF, IGFs, FGFs, TGFs, EGF, VEGF, HGF, IL-6, G-SCF and KGF as well as extracellular matrix proteins such as type I and type III collagens, fibronectin, terascin, glycosaminoglycans, versican, decorin and various other secreted human dermal matrix proteins, which may be useful in repairing physical anomalies and may be included as other active agents in the injectable.

The pharmaceutical formulations may be delivered to a subject via a variety of routes using standard procedures well known to those of skill in the art. For example, such delivery may be site-specific (fingers, toes, ankles, knee and other joints).

Therapeutic products contained in the conditioned media include, but are not limited to, peptides, growth factors, enzymes, hormones, cytokines, antigens, antibodies, dotting factors, and regulatory proteins. Therapeutic proteins include, but are not limited to, inflammatory mediators, argiogenic factors, Factor VIII, Factor IX, erythropoietin, alpha-1 antitrypsin, calcitonin, glucocerebrosidase, human growth hormone and derivatives, low density lipoprotein (LDL), Erythropoietin (EPO), and apolipoprotein E, IL-2 receptor and its antagonists, insulin, globin, immunoglobulins, catalytic antibodies, the interleukins, insulin-like growth factors, superoxide dismutase, immune responder modifiers, BMPs (bone morphogenic proteins) parathyroid hormone and interferon, nerve growth factors, tissue plasminogen activators, and colony stimulating factors. Of course, the medium may be further processed to concentrate or reduce one or more factor or component contained within the medium, for example, enrichment of a growth factor using immunoaffinity chromatography or, conversely, removal of a less desirable component, for any given application as described herein.

Assays commonly employed by those of skill in the art may be utilized to test the activity of the particular factor or factors, thereby ensuring that an acceptable level of biological activity (e.g., a therapeutically effective activity) is retained and/or generated by post-harvest processing. Doses of such therapeutic factors are well known to those of skill in the art and may be found in pharmaceutical compedia such as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publ., THE CHEMOTHERAPY SOURCE BOOK, Williams and Wilkens Publishers.

The therapeutically effective doses of any of the growth factors, drugs or other active agents described above may routinely be determined using techniques well known to those of skill in the art. A "therapeutically effective" dose refers to that amount of the compound sufficient to result in amelioration of at least one symptom of the processes and/or diseases being treated.

Toxicity and therapeutic efficacy of the drugs can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, some of the growth factors secreted into the medium have the following concentrations:
TGF Beta-1 at about 0.01-100 ng/mL, about 0.1-10 ng/mL, or about 1-3 ng/mL.
TGF Beta-2 at about 0.1-1000 pg/mL, about 1-1000 pg/mL, or about 100-160 pg/mL.
TGF Beta-3 at about 0.1-1000 pg/mL, about 1-1000 pg/mL, or about 50-100 pg/mL.
IL-3 at about 0.1-1000 pg/mL, about 1-1000 pg/mL, or about 60 pg/mL.
IL-6 at about 0.1-1000 ng/mL, about 1-100 ng/mL, or about 11 ng/mL.
IL-7 at about 0.1-1000 pg/mL, about 1-100 pg/mL, or about ~50 pg/mL.
IL-8 at about 0.1-1000 ng/mL, about 1-100 ng/mL, or about ~4-10 ng/mL.

In another embodiment, growth factor-enriched conditioned medium from melanocytes and/or other cell types may be combined with conditioned medium from fibroblasts. The concentration of FGF-2 secreted by melanocytes typically ranges from about 10-10,000 pg/mL, about 100-1000 pg/mL, or about 400-450 pg/mL.

In one embodiment, a kit is disclosed including an injectable comprising a hyaluronic acid and conditioned medium or extract or concentrate thereof, from cultured substantially homogenous foreskin derived fibroblast cells, where the conditioned medium is generated by incubating a nutrient medium with the cells in two-dimensional culture under conditions adapted to promote secretion of at least one growth factor into the nutrient medium, and where the at least one growth factor is present in the conditioned medium or extract or concentrate thereof in an amount sufficient to treat or prevent inflammation associated with osteoarthritis; a container; a label; and instructions which provide methods of injecting the composition. The instructions may be a pamphlet, CD, or other computer readable medium. Further, the instructions may provide information about a website which may contain downloadable content.

The following examples are intended to illustrate but not limit the invention.

EXAMPLES

1. Isolation of Human Foreskin Fibroblasts
   I. Materials
   100 mm sterile tissue culture dishes
   150 mm sterile tissue culture dishes
   Sterile scalpel blades
   Sterile full-curved forceps
   Sterile half-curved scissors
   50 ml Centrifuge Tubes
   1, 5, and 10 ml Pipette Tips
   Pipettes
   Dulbecco's Modified Eagle's Medium (DME/High Modified)
   Fetal Bovine Serum (FBS)
   Antibiotic-Antimycotic (ABAM)
   L-Glutamine (L-GLU)
   Phosphate Buffer Saline (PBS)
   Trypsin-EDTA 1× (0.25% Trypsin 1 mM EDTA-4Na. Prepared with 2.5 g Trypsin (250) and 0.38 g EDTA-4Na in 1 liter of HBSS without Ca and Mg++.
   Transport Media:
   ADD to 500 ml bottle of DMEM:
   FBS 50 ml
   ABAM 5 ml
   Growth Media (GM):
   ADD to 500 ml bottle of DMEM: Final Conc.
   FBS 50 ml 10%
   ABAM 5 ml 1%
   L-glu 5 ml 292n/ml.
   II. Isolation Technique
   Foreskins were obtained from newborn babies after circumcision and were donated by their parents. Samples were transported in a sterile centrifuge tube with 5 ml Transport Media at room temperature. The samples were removed from the tube with a sterile pipette and placed in a 100 mm tissue culture dish. The cells were washed three times with PBS-CMF/1% ABAM. Subcutaneous fatty tissue was trimmed with curved scissors and forceps.

The samples were split horizontally into 0.5×1.0 cm² pieces and placed in a 100 mm tissue culture dish with the epidermis side down. Ten ml of Trypsin-EDTA 0.25% and refrigerate (4° C.) overnight (16-18 hrs) was then added.

Samples are taken from the refrigerator and epidermis was separated from dermis using two forceps. Under these conditions the epidermis should peel off easily from dermis. Trypsin exposed single cells were removed and placed in centrifuge tube and 15 ml of GM was added to stop the action of Trypsin. The resulting solution was then centrifuged for 10 minutes at 800×g in a Sorvall Highconic fixed angle rotor.

Fibroblasts were isolated by taking the dermis explants and mincing them into fine pieces, where they were plated on 100 mm petri dishes. The foreskins were washed, minced by scissors, and dissociated to single cells by trypsinization. The resulting cells were grown in a culture medium consisting of 80% Dulbecco's modified Eagle medium (DMEM; no pyruvate, high-glucose formulation) supplemented with either 20% fetal bovine serum (FBS; Hyclone, Logan, Utah); 20% SR; or 20% human serum (Chemicon International, Temecula, Calif.), 2 mM L-glutamine, 0.1 mM β-mercaptoethanol, and 1% nonessential amino acid stock (Gibco Invitrogen Corporation, Carlsbad, Calif.). The foreskin cells were split using trypsin-EDTA (0.5% trypsin and 0.25% EDTA; Gibco Invitrogen) every 5-7 days. Ten ml of fibroblasts media was added to the cells, which were then placed in incubator without disturbance for 48 hours. The cells were passaged and expanded once, where the dishes were at about 50-60% confluent.

Trypsinizing was accomplished by removing the spent media. Five ml of Trypsin 0.25% was added and cells were incubated at 37° C./5% $CO_2$ for 10 minutes. The culture was checked frequently under the microscope to ensure that cells were peeling off. Where necessary, the dishes were tapped on the side to help dislodge cells.

When cell-peeling was confirmed, 5 ml of GM was added to stop the action of Trypsin. Single cells were place in a centrifuge tube and centrifuged for eight minutes at 800×g in a Sorvall Highconic fixed angle rotor. The supernatant was removed and resulting cells were resuspended DMEM with 5%-20% FBS.

2. Method of Cell Culture

This protocol is for use of the wave bioreactor with Nunc MicroHex microcarriers (Nalge Nunc International, Denmark). Nunc MicroHex are 2D, flat hexagonal shaped polystyrene carriers with side lengths of 125 microns.

I. Inoculation

The Cellbag (Wave Biotech) was inflated with air and 10% $CO_2$ until rigid. Media was added and the inlet and outlet filters were clamped. The Cellbag were then rocked at about 15 rocks per minute (rpm) and an angle of about 7 degrees. The temperature and pH were allowed to equilibrate. The initial volume was about 50% of the final culture volume. The microcarriers and cell suspension were then added. Generally, an initial cell density of about 0.1-0.5×10⁶ cells per mL was added. The inlet and outlet filters were kept clamped and rocking was continued at a rate of about 20 rpm and an angle of about 7 degrees. The attachment process was continued over several hours or overnight.

II. Operation

Once the cells were attached, the remaining amount of media was added to bring the culture up to final volume. Cell density, viability, and metabolism were monitored while the cells were growing. The oxygen levels were monitored and the rpm and angle adjusted in response to oxygen demands of the culture. It is best to maintain a low rpm and angle while maintaining sufficient oxygen and keeping the microcarriers/cells suspended. As the cells continued to grow the media eventually became spent. Media exchange was accomplished by shutting off the rocking. With the platform tipped forward, the microcarrier/cell complexes settled to the bottom edge of the Cellbag within minutes. The media was then be pumped out without removing any of the microcarriers. Up to 90% of the culture volume was removed in this manner. Fresh pre-warmed media was added and rocking the Cellbag was resumed at the previous settings.

III. Rocking Speed

The rocking speed was dependent on the culture volume, cell density, and Cellbag size cell or culture flask or petri dish. For Cellbag 2 L and 10 L, the speed was set at about 15 to 20 rpm initially. The speed was increased to about 20 to 25 rpm as the cell density increased.

IV. Rocking Angle

For Cellbag 2 L and 10 L, an initial angle of 6 degrees was sufficient. When max cell density was achieved, an angle of about 7-8 degrees was preferred.

V. Aeration Rate

The Cellbag was kept rigidly inflated. During Cellbag inflation, a flow rate of up to about 0.5 L per minute (1 pm) was used. Once vigorous growth was observed, the flow rate was set to about 0.1 lpm for the 2 L bag, and about 0.2 lpm for the 10 L Cellbag.

VI. Operating Temperature

Typical operating temperature for mammalian cells is 36-37 degrees C.

VII. pH Control pH control is extremely critical. Due to the high gas transfer capacity of the Wave bioreactor, pH may drift rapidly. The following procedure was used:

a. the Cellbag was initially inflated with 10% $CO_2$/air. After inflation, media and microcarriers were added to the bioreactor and the inlet and outlet air filters were closed off. For the pH and temperature to completely equilibrate, the Cellbag was allowed to rock 1-2 hours at about 15 rpm. Before inoculation, the pH was checked by taking a sample and adjusted when necessary.

b. The microcarriers were inoculated with cells, where the inlet and outlet filters remained closed.

c. Monitoring pH, glucose concentration and cell density. Once the pH and glucose levels started dropping, continuous airflow through the headspace was switched to 5% $CO_2$/air. This occurred within 24-60 hours. Once vigorous cell growth occurred, the media pH did not drift upwards and $CO_2$ concentration in the sweep gas functioned to control pH.

d. The rock rate and angle were increased to maintain oxygen concentration.

e. Care was taken when replacing spent media. The pH was monitored and $CO_2$ concentration was adjusted as cells became acclimated to the fresh media.

VIII. Scale Up

A typical scale up for a cell line on Nunc microcarriers is given below:

a. 500 mL media was used to fill a 2 L Cellbag. Thirteen grams of MicroHex carriers was added and pH was allowed to equilibrate. Enough cell inoculum was added to give a starting cell count of at least $0.3 \times 10^6$ cells/mL ($1.5 \times 10^8$ cells total). The rock rate was set at about 15 rpm and at an angle of about 6 degrees overnight. The system was kept at operating temperature.

b. The next day 500 mL of media was added, and the rpm was adjusted to about 18, while the angle was adjusted to about 6 degrees.

c. Culturing was continued for another day until the pH began to drop. The inlet and outlet filters were unclamped and continuous air/$CO_2$ flow was commenced. The oxygen levels in the culture carefully were monitored carefully. The rpm was adjusted to about 20.

d. Culturing was continued for a few more days until glucose levels and low pH indicated that the media was spent. Fifty percent of the media was exchanged, with careful monitoring of the pH. The rpm was adjusted to about 22 and the angle was adjusted to about 7 degrees.

e. The 50% media change was continued every second day.

Formulations

When the cells reached about 80-95% confluence, the conditioned media was then added to the various compositions as set forth below.

AQT JXN

| Ingredient* | Function | Wt % |
|---|---|---|
| Water (Aqua) | Base solvent | 88-78.00 |
| Total growth factors | Cartilage Repair | 1.00 |
| Hyaluronic Acid | Reduce inflammation, cartilage repair | 1.00 |
| Conditioned Media | Growth factors | 10-20% |

Example 1. Study

AQT JXN was formulated as above, with the proviso that the compositions contained 1% total growth factors in a 2 ml dose or 1% total growth factors in a 4 ml dose. The composition was injected into various articulating joints (e.g., knees, ankles, fingers) of human subjects and the following evaluations were performed by a staff RN or staff physician: Visual Analogue Scale, WOMAC Index, Patient Global Impression of Change (PGIC), European Quality of Life 5 Dimension, and Euro Quality of Life Health Index. Follow ups were at 1 month (2 ml dose) and 1 month and 3 months (4 ml dose).

The study was conducted using 32 subjects between the ages of 58.8 to 58.9 yrs old. Volunteers signed comprehensive informed consent documents.

Results

As demonstrated in FIGS. 2-6, patients reported improvements on all evaluations tested. As shown in Table 1, a comparison is made between the 2 and 4 ml doses.

TABLE 1

Summary of 2 ml v. 4 ml Cytokine Solution

| | 2 ml | | 4 ml | |
|---|---|---|---|---|
| Vas | 6.75 (SD 1.41) | 2.75 (SD 2.72) | 6.76 (SD 2.38) | 3.75 (SD 2.50) |
| WOMAC | 51.83 (SD 16.58) | 28.83 (SD 26.24) | 59.76 (SD 22.52) | 34.69 (SD 2.50) |
| PGIC | 5.00 (SD 1.26) | 2.67 (SD 1.75) | 5.18 (SD 1.29) | 3.19 (SD 1.11) |
| EuroQal Idx | 69.17 (SD 20.10) | 84.17 (SD 17.15) | 60.88 (SD 24.38) | 76.69 (13.60) |
| Euro Qual Dimensions | | | | |
| Mobility | 3.33 (SD 0.82) | 2.50 (SD 1.05) | 3.18 (SD 0.81) | 2.44 (SD 0.81) |
| Self-care | 2.17 (SD 1.33) | 1.67 (SD 1.21) | 1.65 (SD 0.93) | 1.38 (SD 0.50) |
| Activities | 2.67 (SD 1.03) | 2.00 (SD 1.10) | 2.82 (SD 1.01) | 2.13 (SD 0.72) |
| Pain | 3.50 (SD 0.55) | 2.50 (SD 1.22) | 3.53 (SD 0.87) | 2.38 (SD 0.72) |
| Anxiety | 2.00 (SD 1.00) | 1.00 (SD 0.00) | 1.65 (SD 0.86) | 1.13 (SD 0.34) |

Based on this data, further studies were continued with the 4 ml dose.

Example 2. 4 ml Dose

AQT JXN was formulated as above, with the proviso that the compositions contained 1% total growth factors in a 4 ml dose. The composition was injected into various joints as above of human subjects and the following evaluations were performed by a staff RN or staff physician: Visual Analogue Scale, WOMAC Index, Patient Global Impression of Change (PGIC), European Quality of Life 5 Dimension, and Euro Quality of Life Health Index. Follow ups were at 3 months.

The study was conducted using 45 subjects between the ages of median age 58 years. Volunteers signed comprehensive informed consent documents.

Results

As shown in FIGS. 7 to 11, patients reported improvements on all evaluations tested. As shown in Table 2, a comparison is made between baseline and at 3 months.

TABLE 2

AQ JNX Effects at Baseline vs. 3 Months

| | Baseline 4 ml | At 3 Months 4 ml | P Value |
|---|---|---|---|
| Vas | 6 (5-9.2) | 3.5 (2-5) | 0.001 |
| WOMAC | 67 (31-81) | 35.5 (23.2-49.5) | 0.001 |
| PGIC | 6 (4-6) | 3.5 (2-4) | 0.002 |
| EuroQal Idx | 65 (50-82.5) | 82.5 (67.5-90) | 0.001 |
| EuroQal Dimensions | | | |
| Mobility | 3 (2.4-4) | 2.5 (2-3) | |
| Self-care | 1 (1-2) | 1 (1-2) | |
| Activities | 3 (2-4) | 2 (2-3) | |
| Pain | 3 (3-4) | 2.5 (2-3) | |
| Anxiety | 1 (1-2.5) | 1 (1-1) | |

Table 3 shows a comparison between AQT JXN and competitors, namely Supartz FX, Hyalgan, Orthovisc, Euflexxa, MonoVisc, Synvisc, Sunvisc One and Gel One.

TABLE 3

Comparison between AQ JNX and other Commercial Treatments

|  | AQ JNX | Supartx FE | Hyalgan | Orthovisc | Efflexxa | Monovisc | Synvisc | Synvisc One | Gel One |
|---|---|---|---|---|---|---|---|---|---|
| HA Concentration | 1% | 1% | 1% | 1% | 1% | 2.2% | 0.8% | 0.8% | 1% |
| Total Volume Per Syringe | 40 mg | 25 mg | 20 mg | 30 mg | 20 mg | 88 mg | 16 mg | 48 mg | 30 mg |
| Injection Regimen | Single | 3 or 5 Weekly | 3 or 5 Weekly | 3-4 Weekly | 3 Weekly | Single | 3 Weekly | Single | Single |
| WOMAC % Improvement | 44.5% at 1 month | 52% at 3 months | 37.5% at 6 months | 51% at pt achieved ≥50% at 5 months | 62% at 3 months | 46% at 6 months | 52% at 6 months | 40% at 6 months | 40% at 6 months |
| Endotoxins | None detectable | 0.5 μg/ml | 4.5 μg/ml | N/A | N/A | N/A | 7.5 μg/ml | 7.5 μg/ml | N/A |

Figure 12:
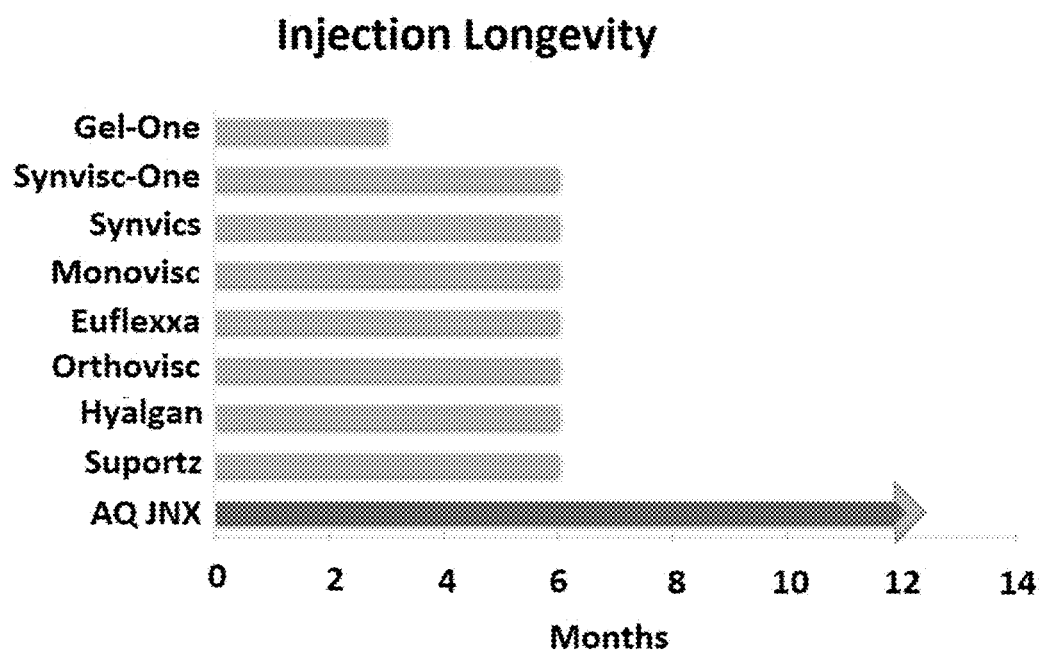
FIG. 12 shows injection longevity of AQ JNX compared to competitor compositions.

As shown in FIG. 12, the effects of AQ JNX last about 12 months or more.

CONCLUSIONS

Advantages of the AQ JNX include that is may be applied as a single injection for efficacy, longevity of greater than or equal to 12 months, no detectable endotoxins, lower viscosity solution (makes for easier and faster injections), cartilage regeneration, and improved Quality of Life (QOL).

While a number of preferred embodiments of the invention and variations thereof have been described in detail, other modifications and methods of using and applications for the same will be apparent to those of skill in the art. Accordingly, it should be understood that various applications, modifications, materials, and substitutions may be made of equivalents without departing from the spirit of the invention or the scope of the claims. It should be understood that the invention is not limited to the embodiments set forth herein for purposes of exemplification, but is to be defined only by a fair reading of the appended claims, including the full range of equivalency to which each element thereof is entitled. All references recited herein are incorporated by reference herein in their entireties.

We claim herein:

1. An injectable composition for treating osteoarthritis, comprising non-crosslinked hyaluronic acid (HA), wherein said HA has a molecular weight of about 300,000 daltons, and a conditioned medium or extract or concentrate thereof, from cultured substantially homogenous fibroblast cells, wherein said conditioned medium is generated by incubating a nutrient medium with said cells in two-dimensional culture under conditions adapted to promote secretion of at least one growth factor into the nutrient medium, and wherein said at least one growth factor is present in said conditioned medium or extract or concentrate thereof in an amount sufficient to treat osteoarthritis symptoms, and wherein said composition does not cause inflammation at a therapeutically effective dose.

2. The composition of claim 1, wherein said cells are from a cell line designated as ATCC Accession No. PTA-11680.

3. The composition of claim 1, wherein the therapeutically effective dose is between about 0.25% growth factors/ml to about 0.5% growth factors/ml.

4. The composition of claim 1, wherein the at least one growth factor is selected from the group consisting of EGF, PDGF, FGF, TGF-β, TGF-α, NGF, Epo, IGF-I, IGF-II, IL-1-α, IL-1-β, IL-2, IL-3, IL-4, IL-5, IL-6, IL-7, IL-8, IL-9, IL-10, IL-11, IL-12, IL-13, INF-α, INF-β, INF-γ, TNF-α, TNF-β, GM-CSF, and M-CSFs, or a combination thereof.

5. The composition of claim 4, wherein the combination comprises TGF Beta-1, TGF Beta-2, TGF Beta-3, IL-3, IL-6, IL-7, and IL-8, and wherein said conditioned media is present at a concentration of at least about 10 to about 20% (wt %).

6. The composition of claim 5, wherein the combination comprises about 1-3 ng/mL TGF β-1, about 100-600 pg/mL TGF β-2, about 50-100 pg/mL TGF β-3, about 60 pg/mL IL-3, about 11 pg/mL IL6, about 50 pg/mL IL-7, and about 4-10 pg/mL IL-8, and wherein said conditioned media is present at about 10% or about 20% (wt %).

7. The composition of claim 1, further comprising a pharmaceutically acceptable carrier.

8. The composition of claim 1, further comprising a second conditioned medium or extract or concentrate thereof, wherein the second conditioned medium is generated by incubating a nutrient medium with a second substantially homogeneous eukaryotic cell type in two-dimensional culture under conditions adapted to promote secretion of at least one second growth factor or one or more extracellular matrix proteins, and wherein said growth factors or extracellular matrix proteins are present in said conditioned medium or extract or concentrate thereof in amounts sufficient to treat symptoms associated with osteoarthritis.

9. The composition of claim 1, wherein said symptoms are selected from the group consisting of joint pain, joint stiffness, joint swelling, limited range of motion of joints, bony growths at the edge of joints, and combinations thereof.

10. The composition of claim 1, wherein the conditions comprise culturing of said cells with two-dimensional polysterene microcarriers.

11. A kit comprising: a) the composition of claim 1; b) a container; c) a label; and d) instructions which provide methods for injecting the composition.

12. The composition of claim 11, further comprising at least one preservative.

13. A method of treating a symptom associated with osteoarthritis comprising: injecting into a joint of a subject in need thereof the composition of claim 1 comprising a conditioned medium or extract or concentrate thereof, from cultured substantially homogenous foreskin derived fibroblast cells, wherein said conditioned medium is generated by incubating a nutrient medium with said cells in two-dimensional culture under conditions adapted to promote secretion of at least one growth factor into the nutrient medium, and wherein said at least one growth factor is present in said conditioned medium or extract or concentrate thereof in an amount sufficient to treat a symptom associated with osteoarthritis.

14. The method of claim 13, wherein the site of injection is the hips, knees, fingers, feet, toes or ankles.

15. The method of claim 13, wherein a single injection is effective for at least a year.

16. The method of claim 13, wherein the symptom is selected from the group consisting of joint pain, joint stiffness, joint swelling, limited range of motion of joints, bony growths at the edge of joints, and combinations thereof.

17. The method of claim 13 wherein the at least one growth factor is selected from the group consisting of EGF, PDGF, FGF, TGF-β, TGF-α, NGF, Epo, IGF-I, IGF-II, IL-1-α, IL-1-β, IL-2, IL-3, IL-4, IL-5, IL-6, IL-7, IL-8, IL-9, IL-10, IL-11, IL-12, IL-13, INF-α, INF-β, INF-γ, TNF-α, TNF-β, GM-CSF, and M-CSFs, or a combination thereof.

18. The method of claim 17, wherein the combination comprises TGF β-1, TGF β-2, TGF β-3, IL-3, IL-6, IL-7, and IL-8, and wherein said conditioned media is present at a concentration of at least about 5-20% (wt %).

19. The method of claim 18, 1-3 ng/mL TGF β-1, about 100-600 pg/mL TGF β-2, about 50-100 pg/mL TGF β-3, about 60 pg/mL IL-3, about 11 pg/mL IL6, about 50 pg/mL IL-7, and about 4-10 pg/mL IL-8, and wherein said conditioned media is present at a concentration of at least about 10% (wt %).

20. The method of claim 13, wherein the composition further comprises a second conditioned medium or extract or concentrate thereof, wherein the second conditioned medium is generated by incubating a nutrient medium with a second substantially homogeneous eukaryotic cell type in two-dimensional culture under conditions adapted to promote secretion of at least one second growth factor or one or more extracellular matrix proteins, and wherein said growth factors or extracellular matrix proteins are present in said conditioned medium or extract or concentrate thereof in amounts sufficient to treat the symptom associated with osteoarthritis.

\* \* \* \* \*